United States Patent
Michel et al.

(10) Patent No.: US 11,944,698 B2
(45) Date of Patent: Apr. 2, 2024

(54) DISPERSION WITH A DISPERSED FATTY PHASE HAVING A HIGH PIGMENT CONTENT

(71) Applicant: CAPSUM, Marseilles (FR)

(72) Inventors: Cassia Michel, Marseilles (FR); Laurence Rehault, Orleans (FR)

(73) Assignee: CAPSUM, Marseilles (FR)

( * ) Notice: Subject to any disclaimer, the term of this patent is extended or adjusted under 35 U.S.C. 154(b) by 0 days.

(21) Appl. No.: 16/647,359

(22) PCT Filed: Sep. 14, 2018

(86) PCT No.: PCT/EP2018/074978
§ 371 (c)(1),
(2) Date: Mar. 13, 2020

(87) PCT Pub. No.: WO2019/053236
PCT Pub. Date: Mar. 21, 2019

(65) Prior Publication Data
US 2021/0022970 A1     Jan. 28, 2021

(30) Foreign Application Priority Data
Sep. 14, 2017  (FR) .................................. 17 58539

(51) Int. Cl.
| | |
|---|---|
| *A61K 8/11* | (2006.01) |
| *A61K 8/04* | (2006.01) |
| *A61K 8/36* | (2006.01) |
| *A61K 8/898* | (2006.01) |
| *A61Q 1/02* | (2006.01) |

(52) U.S. Cl.
CPC ................ *A61K 8/11* (2013.01); *A61K 8/042* (2013.01); *A61K 8/361* (2013.01); *A61K 8/898* (2013.01); *A61Q 1/02* (2013.01); *A61K 2800/43* (2013.01)

(58) Field of Classification Search
CPC ... A61Q 5/00; A61Q 1/02; A61Q 9/00; A61K 8/361; A61K 8/042; A61K 2800/43; A61K 2800/437; A61K 8/11; A61K 8/04; A61K 8/898
See application file for complete search history.

(56) References Cited

U.S. PATENT DOCUMENTS

| | | |
|---|---|---|
| 5,874,069 A | 2/1999 | Mendolia et al. |
| 5,919,441 A | 7/1999 | Mendolia et al. |
| 5,981,680 A | 11/1999 | Petroff et al. |

(Continued)

FOREIGN PATENT DOCUMENTS

| | | |
|---|---|---|
| CA | 796210 A | 10/1968 |
| CN | 103491808 A | 1/2014 |

(Continued)

OTHER PUBLICATIONS

International Search Report for PCT/EP2018/074978 dated Nov. 6, 2018.

(Continued)

*Primary Examiner* — Jianfeng Song
(74) *Attorney, Agent, or Firm* — Pearne & Gordon LLP

(57) ABSTRACT

The invention relates in general to dispersions with a high pigment content, as well as to the uses thereof in the cosmetic industry, and in particular to uses thereof as a makeup composition and particularly as foundation.

14 Claims, 1 Drawing Sheet

(56) References Cited

U.S. PATENT DOCUMENTS

| | | | |
|---|---|---|---|
| 6,051,216 A | 4/2000 | Barr et al. | |
| 9,277,759 B2 | 3/2016 | Bibette et al. | |
| 9,763,862 B2 | 9/2017 | Schmitt et al. | |
| 9,993,398 B2 | 6/2018 | Goutayer et al. | |
| 10,350,567 B2 | 7/2019 | Carreras et al. | |
| 10,600,006 B1 | 3/2020 | Wang et al. | |
| 2005/0287100 A1* | 12/2005 | Lebre | A61K 8/8152 424/70.16 |
| 2007/0185281 A1 | 8/2007 | Song et al. | |
| 2013/0195773 A1* | 8/2013 | Kindel | A61Q 19/04 424/59 |
| 2014/0011033 A1 | 1/2014 | Carreras et al. | |
| 2014/0045949 A1* | 2/2014 | Goutayer | A61K 47/32 514/772.6 |
| 2014/0086861 A1 | 3/2014 | Goldlum et al. | |
| 2015/0164775 A1 | 6/2015 | Julien et al. | |
| 2015/0272861 A1* | 10/2015 | Mazur | A61Q 17/04 424/59 |
| 2019/0060186 A1 | 2/2019 | Goutayer et al. | |
| 2023/0233422 A1 | 7/2023 | Goutayer et al. | |

FOREIGN PATENT DOCUMENTS

| | | |
|---|---|---|
| EP | 2100582 A1 | 9/2009 |
| FR | 2792190 A1 | 10/2000 |
| FR | 2992232 A1 | 12/2013 |
| FR | 2999921 A1 | 6/2014 |
| FR | 3041250 A1 | 3/2017 |
| FR | 3041251 A1 | 3/2017 |
| FR | 3085121 A1 | 2/2020 |
| JP | H02295912 A | 12/1990 |
| WO | 0247619 A2 | 6/2002 |
| WO | 02056847 A1 | 7/2002 |
| WO | 2010063937 A1 | 6/2010 |
| WO | 2012120043 A2 | 9/2012 |
| WO | 2012120098 A2 | 9/2012 |
| WO | 2015055748 A1 | 4/2015 |
| WO | 2015089750 A1 | 6/2015 |
| WO | 2017046305 A1 | 3/2017 |
| WO | 2021234135 A1 | 11/2021 |

OTHER PUBLICATIONS

Search Report for French Application No. FR 17 58539 dated Jan. 9, 2018.

Lubrizol, "Merquat™ 550 Polymer"; Safety Data Sheet, SDS_US—MERQUAT™ 550 POLYMER; pp. 1-9, Feb. 19, 2016.

Tinci, "Cationic Starch"; Doc No. Tc-Mm—***; one page, Version: A/0; last version date: Jan. 28, 2013.

Azelis, "Luviquat Supreme AT 1"; BASF Personal Care—Ross Organic an Azelis company; https://rossorg.com/product/luviquat-supreme-at-1/; pp. 1-3; Mar. 27, 2023.

Stepan S., "Pearlescent Conditioning Shampoo and Body Wash"; Formulation, Revision Date: Dec. 19, 2016 Publication Date: Mar. 7, 2008 @ 2016, Stepan Company.

Dow, "Ucare™ Polymer JR-400", https://www.dow.com/en-us/pdp.ucare-polymer-jr-400.084959z.html#overview, pp. 1-3, Mar. 23, 2023.

Chembk, "1,3-Bis(dimethylamino)propane", https://www.chembk.com/en/chem/1,3-Bis(dimethylamino)propane; pp. 1-3, Mar. 27, 2023.

Solvay, "Jaguar®"; https://www.solvay.com/en/product/jaguar-c-17; pp. 1-4, Mar. 27, 2023.

Solvay, "Mirapol® A 15"; https://www.solvay.com/en/product/mirapol-15; pp. 1-4, Mar. 27, 2023.

Lubrizol, "Merquat™ 550PR Polymer"; Technical Data Sheet; TDS-821, pp. 1-2; Feb. 23, 2012.

Universal Selector, "Lamequat® L Properties"; http://cosmetics.specialchem.com; pp. 1-2, May 7, 2021.

* cited by examiner

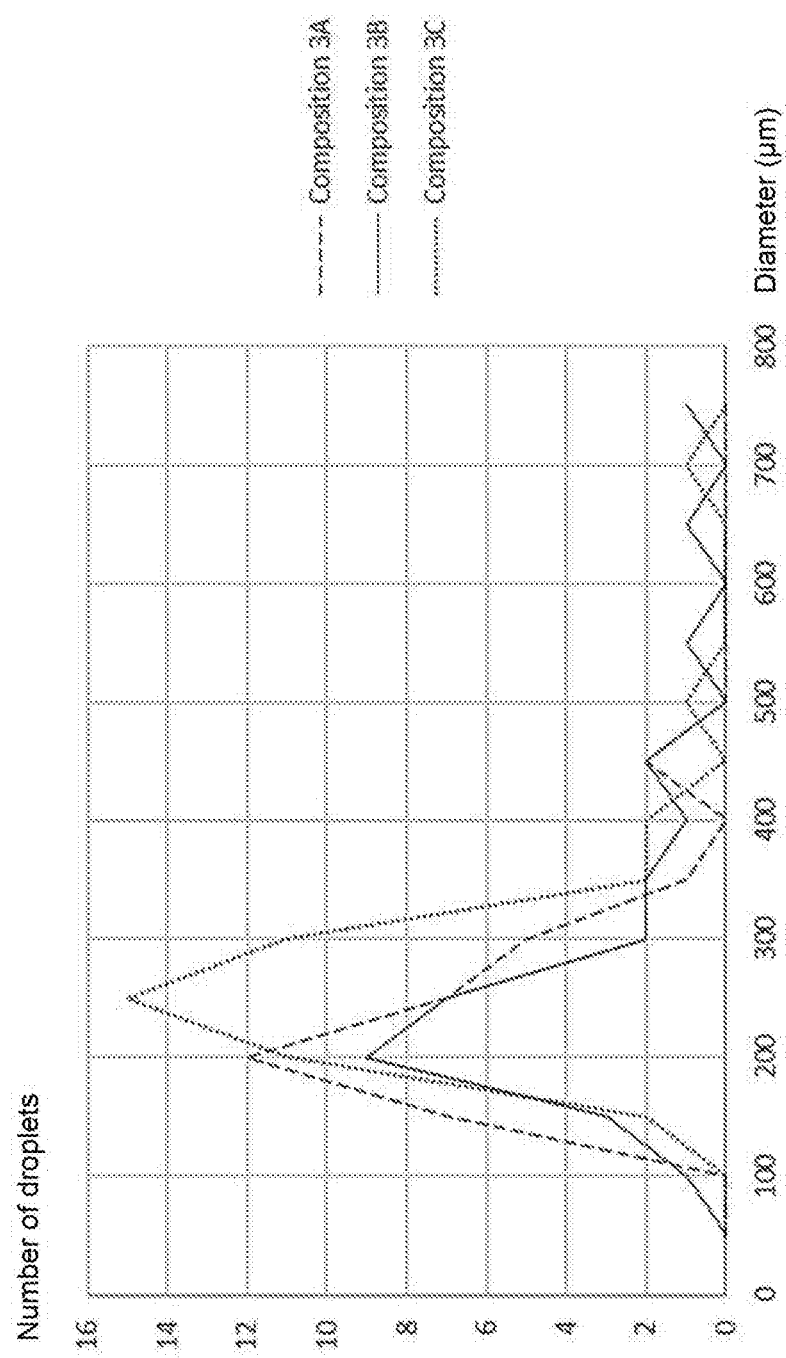

DISPERSION WITH A DISPERSED FATTY PHASE HAVING A HIGH PIGMENT CONTENT

CROSS-REFERENCE TO RELATED APPLICATIONS

This is a National Stage application of PCT international application PCT/EP2018/074978, filed on Sep. 14, 2018, which claims the priority of French Patent Application No. 17 58539, Sep. 14, 2017, both of which are incorporated herein by reference in their entirety.

The present invention generally relates to dispersions having a high pigment content and to uses thereof in the cosmetic field, and in particular uses thereof as makeup composition in particular as foundation.

One of the main objectives in cosmetics is to enhance the outer appearance of the skin, the face in particular. In general, foundations are used to improve characteristics or to hide skin imperfections. These foundations are generally available in the form of liquid or semi-liquid suspensions, or creams, emulsions, gels as well as pressed powders, anhydrous oils and wax compositions.

There is a need to develop novel cosmetic compositions, make-up compositions in particular, which afford a novel sensorial experience for users and/or which are more efficient. Formulations have been developed in recent years in the form of macroscopic dispersions, in particular such as described in WO2012120043 and WO2015055748. These macroscopic dispersions impart a differentiating, highly attractive visual appearance whilst protecting the encapsulated active substances. Nonetheless, existing macroscopic dispersions are in general scarcely or not at all coloured and are used as care products which have insufficient colouring or colouring capacity of keratin material.

A few coloured macroscopic dispersions comprising colouring agents (colouring chemical substance soluble in the coloured particle) or pigments (colouring chemical substance in powder form and insoluble) have been described, for example in FR3041250. However, the colouring agent or pigment content thereof, in particular in dispersed phase, is very low which means they are little adapted for use as make-up composition. In addition, these low contents of colouring agents or pigments are such that the corresponding cosmetic products have properties in terms of coverage that are unsatisfactory.

On account of their powdery, insoluble nature, pigments are difficult to integrate in the dispersed phase of dispersions. In addition, in the rare cases in which it is possible to formulate a macroscopic dispersion comprising a pigment, it is observed that undesired phenomena occur such as sedimentation of the pigments inside the droplets of said dispersion.

It often proves to be complicated therefore to add high contents of pigments to emulsified systems, in particular in dispersed phases, without deteriorating the stability and sensory feel thereof and the quality of the film deposited on keratin material and particularly on the skin. It is also difficult to reconcile opposing aspects of technical performance in one same composition such as coverage, feeling of freshness even hydration. These problems are further exacerbated if a dispersion is considered comprising a dispersed phase in the form of droplets of macroscopic size.

Therefore, concerning makeup foundations, priority is given to emulsifying systems which are chiefly inverse emulsions with pigments in continuous phase having regard to the good level of coverage and homogenous appearance they provide compared with direct emulsions. Their weak point on the other hand is a strong sensation of oiliness and tackiness and/or lack of freshness and natural appearance, and hence lack of lightness of the textures obtained. The few emulsifying systems of «direct emulsion» type currently on the market comprise pigments that are generally in continuous aqueous phase imparting thereto poor resistance to sweat and moisture.

It therefore remains difficult for persons skilled in the art to propose compositions able to impart a long-lasting visual result on the skin with sensations of lightness and freshness together with good hydration on application, this expected visual result preferably being flawless coverage of colour imperfections and/or surface imperfections.

There is therefore a need for a cosmetic alternative which gives users full satisfaction first with regard to colour and coverage of imperfections and secondly with regard to sensory feel, freshness, hydration and lightness, free of any feelings of oiliness or tack on application which is smooth and has good slip.

The inventors have unexpectedly found that said objectives can be reached with a dispersion of the invention.

More specifically the inventors have found that a dispersion of the invention allows a significant number of technical achievements to be grouped together in a single dispersion, advantageously without the hold and/or intensity of each one being attenuated by the performance of the others, and even in some cases being stimulated thereby.

The invention therefore concerns a dispersion containing a dispersed phase comprising droplets (called «droplets (G1)») and a continuous aqueous phase, preferably in gel form, in which the droplets comprise at least one fatty phase and optionally a shell, said shell comprising at least one anionic polymer and at least one cationic polymer, characterized in that the fatty phase comprises at least one pigment in a content higher than 23.5 weight % relative to the weight of said fatty phase.

If several pigments are contained in the fatty phase, this weight proportion is the accumulated proportion of pigments. These proportions are expressed in relation to the weight of the fatty phase contained in the dispersed phase.

As arises from the following examples, the inventors have observed that a dispersion of the invention is advantageous in terms of stability, resistance over time, flawless coverage of colour imperfections and/or surface imperfections combined with a sensation of lightness, freshness and hydration on application which has good slip without any sensation of oiliness and/or tack.

In addition, and against all expectations, the inventors have observed that a dispersion of the invention gives a unique and hence improved colour shade on application, with an evolving or progressive makeup result.

By «unique/improved colour shade», it is meant to designate a dispersion of the invention which, when applied in equivalent pigment type and content onto keratin material in particular the skin, forms a film on said keratin material having a darker shade than a conventional foundation composition in particular in emulsion form. In other words, and without wishing to be bound by any theory, a dispersion of the invention appears to allow more efficient visibility of pigments. This advantage particularly provides:

access to colour shades that cannot be reached with conventional compositions; and/or subtle revealing of colour on application.

By «progressive or evolving makeup result», it is meant to designate a dispersion of the invention which, when applied to keratin material and in particular the skin, forms a film having colouring that is not or only slightly intense, this intensity gradually increasing over a short period of time i.e. a period of time longer than 15 seconds, preferably longer than 30 seconds, and less than 120 seconds even less than 90 seconds, and in particular less than 60 seconds.

In conclusion, a dispersion of the invention has unique makeup properties.

The dispersion of the invention has the advantage of being stable in particular over time and during transport. By «stable», in the meaning of the present invention it is meant that there is no creaming or sedimentation of the fatty phase droplets dispersed in the continuous phase, no opacification of the continuous aqueous phase, no aggregation between droplets and in particular no coalescence or Oswald ripening of the droplets, no leakage of material from the dispersed fatty phase towards the continuous phase, or conversely, no diffusion and/or sedimentation of pigments in the fatty phase.

The droplets (G1) of a dispersion of the invention are advantageously macroscopic droplets i.e. visible to the naked eye. Therefore, in one embodiment the droplets have a diameter equal to or larger than 150 µm and represent a volume equal to or greater than 60%, even equal to or greater than 70%, preferably equal to or greater than 80%, and better still equal to or greater than 90% of the total volume of the dispersed phase, and/or at least 60%, even at least 70%, preferably at least 80%, and better still at least 90% of the droplets have a mean diameter equal to or larger than 150 µm, preferably equal to or larger than 250 µm, in particular equal to or larger than 500 µm, even equal to or larger than 1 000 µm, and better still between 150 µm and 3 000 µm, preferably between 250 µm and 2 000 µm, and in particular between 500 µm and 1 500 µm. Therefore, the droplets advantageously have apparent monodispersity, namely that they are seen as spheres of identical diameter. The droplets are advantageously substantially spherical.

The inventors have observed that an increase in the mean diameter of the droplets G1 is correlated with an improvement in the aforementioned advantages of a dispersion of the invention.

In the present invention the aforementioned dispersions can indifferently be termed "emulsions".

The invention also concerns a composition comprising at least one dispersion such as defined above.

Unless otherwise stated, in the entire description it is considered that temperature is ambient temperature (e.g. T=25° C.±2° C.) and pressure is atmospheric (760 mm de Hg, i.e. 1,013.105 Pa or 1 013 mbar).

Viscosity

The viscosity of a dispersion, even of a composition of the invention, can vary extensively which allows different textures to be obtained In one embodiment, a dispersion of the invention has a viscosity of 1 mPa·s to 500 000 mPa·s, preferably of 10 mPa·s to 300 000 mPa·s, better still of 400 mPa·s to 100 000 mPa·s, and more particularly of 1 000 mPa·s to 30 000 mPa·s, as measured at 25° C.

Viscosity is measured at ambient temperature e.g. T=25° C.±2° C. and at ambient pressure e.g. 1013 mbar, following the method described in WO2017046305.

Architecture of the Dispersion

A dispersion of the invention is liquid at ambient temperature and ambient pressure. In other words, a dispersion of the invention is not in solid form particularly a compact or powder form or cast as a stick.

The droplets G1 of a dispersion of the invention can be monophase or multiphase. Therefore, the droplets comprise a core (comprising at least one fatty phase) and optionally a shell (or membrane) fully encapsulating the core. The core is preferably liquid at 25° C. The core may itself comprise one or more phases. In general, the at least one pigment is contained in the phase (one of the phases) of the core.

In one embodiment, the droplets of a dispersion of the invention comprise a core that is liquid or at least partly gelled or at least partly thixotropic, and optionally a shell fully encapsulating said core, said core being monophase and in particular containing a fatty (or oily) phase. Said type of droplets leads to a simple dispersion comprising two separate phases, an inner liquid phase or partly gelled or at least partly thixotropic represented by at least the fatty phase, and an outer aqueous phase preferably in the gelled state surrounding the inner phase.

In another particular embodiment, the droplets of a dispersion of the invention comprise a core that is liquid or at least partly gelled or at least partly thixotropic, and optionally a shell fully encapsulating said core, said core comprising an intermediate droplet of an intermediate phase, the intermediate phase being placed in contact with the continuous aqueous phase or the shell if provided, and at least one preferably a single inner droplet of an inner phase being arranged in the intermediate droplet, at least one of the intermediate and/or inner phase(s) forming the fatty phase, and the pigment(s) being contained in the intermediate phase and/or inner phase.

Advantageously, the intermediate phase is oily and the inner phase is aqueous or formed of a different oily phase non-miscible at ambient temperature and pressure with said intermediate phase. Said type of droplets leads to a complex dispersion meaning that the liquid, viscous or thixotropic core comprises a single intermediate droplet of an intermediate phase, the intermediate phase being placed in contact with the continuous aqueous phase or with the shell if provided, and at least one preferably a single inner droplet of an inner phase arranged in the intermediate droplet.

In one variant, the core comprises a continuous intermediate phase in which there is a plurality of droplets of inner phases(s).

In one particular embodiment:
the continuous aqueous phase can be in the form of a direct emulsion (oil-in-water), said emulsion comprising a continuous aqueous phase and a fatty phase dispersed in the form of droplets (G2), the size of the droplets (G2) preferably being smaller than the size of droplets (G1);
and/or
the fatty phase, even the intermediate phase and/or the inner phase for a complex dispersion such as defined above, can be in the form of an inverse emulsion (water-in-oil), said emulsion comprising a continuous fatty phase and an aqueous phase dispersed in the form of droplets (G3), the size of droplets (G3) necessarily being smaller than the size of droplets (G1) and preferably being microscopic.

In particular, the size of droplets (G2) and/or (G3) is smaller than 500 µm, preferably smaller than 400 µm, in particular smaller than 250 µm, most particularly smaller than 150 µm, further particularly smaller than 100 µm, even smaller than 20 µm, and better still smaller than 10 µm. Preferably the size of droplets (G2) and/or (G3) is between 0.1 µm and 200 µm, preferably between 0.25 µm and 100 µm, in particular between 0.5 µm and 50 µm, preferably between 1 µm and 20 µm, and better still between 1 µm and 10 µm, even between 3 µm and 5 µm.

Optionally, droplets (G2) and/or (G3) comprise a shell formed of at least one anionic polymer, in particular a carbomer, and of at least one cationic polymer, in particular an amodimethicone, said anionic and cationic polymers being such as defined below.

Advantageously, droplets (G2) and/or (G3) are not macroscopic, and are therefore microscopic i.e. non visible to the naked eye.

In other words, droplets (G2) and/or (G3) are different and independent of droplets (G1).

These droplets (G2) and/or (G3) of reduced size allow an effect to be obtained on texture. A dispersion of the invention comprising said finely dispersed droplets (G2) and/or (G3) has improved qualities of smoothness.

The presence of droplets (G2) and/or (G3) strengthens the characteristics of a dispersion of the invention in terms of unique texture, lightness and evolving sensory feel. More particularly, a dispersion of the invention comprising droplets (G2) and/or (G3) spreads easily over keratin material, the skin in particular. This texture is particularly advantageous and surprising for skilled persons. Advantageously droplets (G2) and/or (G3) can also comprise at least one pigment, the same or differing from the pigment(s) contained in the fatty phase of droplets (G1).

Advantageously, the intermediate phase also comprises at least one gelling agent, in particular such as defined below. The gelling agent contributes in particular to improving the suspension of the inner droplet(s) arranged in the intermediate droplets of the droplets of a dispersion of the invention according to this embodiment. In other words, the gelling agent can prevent/avoid phenomena of creaming or sedimentation of the inner droplet(s) arranged in the intermediate droplet of droplets (G1) of a dispersion of the invention according to this embodiment.

Continuous Aqueous Phase

In one embodiment, the aqueous phase has viscosity of between 400 mPa·s and 100 000 mPa·s, preferably between 800 mPa·s and 30 000 mPa·s, as measured at 25° C.

This viscosity is measured following the method described above.

The continuous phase of the dispersions comprises water. In addition to distilled or deionised water, water suitable for the invention can also be a natural spring water or floral water.

In one embodiment, the weight percent of water in the continuous aqueous phase is at least 30%, preferably at least 40%, in particular at least 50%, and better still at least 60%, particularly between 70% and 98%, and preferably between 75% and 95%, relative to the total weight of said continuous phase.

The continuous aqueous phase of the dispersion of the invention may also comprise at least one base. It can comprise a single base of mixture of several different bases. The presence of at least one base in said continuous aqueous phase contributes in particular towards enhancing the viscosity thereof.

In one embodiment, the base contained in the aqueous phase is a mineral base.

In one embodiment, the mineral base is selected from the group formed by alkali metal hydroxides and alkaline-earth metal hydroxides.

Preferably the mineral base is an alkali metal hydroxide and NaOH in particular.

In one embodiment, the base contained in the aqueous phase is an organic base. Among organic bases, mention can be made for example of ammonia, pyridine, triethanolamine, aminomethyl propanol, or triethylamine.

A dispersion of the invention may comprise from 0.01 to 10 weight %, preferably 0.01 to 5 weight %, more preferably 0.02 to 1 weight % of base, preferably a mineral base and NaOH in particular, relative to the total weight of said dispersion.

Preferably, the continuous aqueous phase, even the dispersion of the invention, does not comprise a surfactant.

Shell of the Droplets

The droplets (G1) of the dispersed fatty phase can advantageously comprise a shell comprising at least one anionic polymer and at least one cationic polymer.

In the invention, the droplets obtained can have a very thin shell, in particular having a thickness of less than 1% the diameter of the droplets.

The thickness of the shell is therefore preferably less than 1 μm and hence too small to be measured using optical methods.

In one embodiment, the thickness of the shell of the droplets is less than 1 000 nm, in particular between 1 and 500 nm, preferably less than 100 nm, advantageously less than 50 nm, preferably less than 10 nm.

Measurement of the thickness of the shell of the droplets of the invention can be performed using Small-Angle X-ray Scattering, such as reported in Sato et al. J. Chem. Phys. 111, 1393-1401 (2007).

To do so, the droplets are produced using deuterated water, then washed three times with deuterated oil e.g. a deuterated oil of hydrocarbon type (octane, dodecane, hexadecane).

After washing, the droplets are transferred to the Neutron cell to determine the I(q) spectrum; q being the wave vector.

From this spectrum, conventional analyses (REF) are performed to determine the thickness of the hydrogenated (non-deuterated) shell.

Therefore, no resistance related to rupture of the shell is felt by a user when applying to keratin material, and no residual deposit of said shell is ascertained. The term evanescent shell is used.

The droplets of a dispersion of the invention, through the nature and properties of their shells, therefore differ from solid capsules i.e. capsules having a solid membrane such as those described for example in WO2010/063937.

The shell surrounding the droplets of the dispersed phase notably imparts sufficient strength to the droplets and thereby reduces and even prevents the coalescence thereof.

This shell is typically formed by coacervation, i.e. by precipitation of polymers carrying opposite charges. Within a coacervate, the bonds linking together the charged polymers are of ionic type, and are generally stronger than the bonds within a membrane of surfactant type.

The shell is formed by coacervation of at least two opposite charged polymers (or polyelectrolytes) preferably in the presence of a first polymer of cationic type and a second polymer differing from the first polymer of anionic type. These two polymers act as rigidifying agents for the membrane.

The forming of the coacervate between these two polymers can be brought about by modifying the conditions of the reaction medium (temperature, pH, concentration of reagents, etc.).

The coacervation reaction results from neutralisation of these two polymers of opposite charge and allows the formation of a membrane structure via electrostatic interactions between the anionic polymer and cationic polymer. The membrane thus formed around each droplet typically forms a shell fully encapsulating the core of the droplet, thereby isolating the core of the droplet from the continuous aqueous phase.

Advantageously, one of the first and second charged polymers is a lipophilic polymer able to be ionised in contact with an aqueous phase, the other of the first and second charged polymers is a hydrophilic polymer able to be ionised.

Anionic Polymer

In the present invention, by "polymer of anionic type" or «anionic polymer» it is meant a polymer comprising chemical functions of anionic type. The term anionic polyelectrolyte can also be used.

By "chemical function of anionic type", it is meant an AH chemical function capable of yielding a proton to give a function $A^-$. Depending on the conditions of the medium in which it is contained, a polymer of anionic type therefore comprises chemical functions in AH form or else in the form of its conjugated base $A^-$.

As example of chemical functions of anionic type, mention can be made of carboxylic acid functions —COOH, optionally in the form of a carboxylate anion —COO$^-$.

As example of polymer of anionic type, mention can be made of any polymer formed by polymerisation of monomers of which at least one part carries chemical functions of anionic type, such as carboxylic acid functions. Said monomers are for example acrylic acid, maleic acid or any ethylenically unsaturated monomer comprising at least one carboxylic acid function. For example, it may be an anionic polymer comprising monomer units comprising at least one chemical function of carboxylic acid type.

Preferably, the anionic polymer is hydrophilic i.e. soluble or dispersible in water.

Among examples of a polymer of anionic type suitable for implementing the invention, mention can be made of copolymers of acrylic acid or maleic acid with other monomers such as acrylamide, alkyl acrylates, $C_5$-$C_8$ alkyl acrylates, $C_{10}$-$C_{30}$ alkyl acrylates $C_{12}$-$C_{22}$ alkyl methacrylates, methoxy poly(ethylene glycol) methacrylates, hydroxyester acrylates, crosspolymer acrylates, and mixtures thereof.

In the invention, a polymer of anionic type is preferably a carbomer such as described below. This polymer can also be an acrylates/$C_{10-30}$ alkyl acrylate Crosspolymer (INCI name).

In one embodiment, the shell of the droplets comprises at least one anionic polymer e.g. a carbomer.

In the invention and unless otherwise stated, by "carbomer" it is meant an optionally crosslinked homopolymer derived from polymerisation of acrylic acid. It is therefore an optionally crosslinked poly(acrylic acid). Among the carbomers of the invention, mention can be made of those marketed under the trade names Tego® Carbomer 340FD by Evonik, Carbopol® 981 by Lubrizol, Carbopol ETD 2050 by Lubrizol, or Carbopol Ultrez 10 by Lubrizol.

In one embodiment by "carbomer" or "Carbopol®" it is meant a polymer of acrylic acid of high molecular weight crosslinked with allylic sucrose or pentaerythritol allyl ethers (Handbook of Pharmaceutical Excipients, 5th Edition, pill). For example, it is Carbopol®910, Carbopol®934, Carbopol®934P, Carbopol®940, Carbopol®941, Carbopol®71G, Carbopol®980, Carbopol®971P or Carbopol®974P. In one embodiment, the viscosity of said carbomer is between 4 000 and 60 000 cP at 0.5% w/w.

Carbomers have other names: polyacrylic acids, carboxyvinyl polymers or carboxy polyethylenes.

A dispersion of the invention may comprise from 0.01 to 5% by weight, preferably from 0.05% to 2%, more preferably from 0.10% to 0.5%, of anionic polymer(s) in particular carbomer(s) relative to the total weight of said dispersion.

In the invention, the dispersion of the invention may comprise a carbomer and an acrylates/$C_{10-30}$ alkyl acrylate Crosspolymer.

The aqueous phase of the invention may also comprise at least one crosslinked polymer or at least one crosslinked copolymer, said crosslinked polymer or crosslinked copolymer comprising at least one unit derived from polymerisation of one of the following monomers: acrylic or methacrylic acid, alkyl acrylate or methacrylate having 1 to 30 carbon atoms, or the salts thereof.

This is particularly the case when a dispersion of the invention comprises at least one fragrance such as defined below.

The aqueous phase may also comprise a mixture of crosslinked polymers or mixture of crosslinked copolymers, or a mixture of crosslinked polymer(s) and crosslinked copolymer(s).

In the invention, the term "unit derived from polymerisation of a monomer" it is meant that the polymer or copolymer is a polymer or copolymer obtained by polymerisation or copolymerisation of said monomer.

In one embodiment, the crosslinked polymer or crosslinked copolymer is a crosslinked polyacrylate.

The crosslinked copolymers and polymers of the invention are anionic.

In one embodiment, the copolymer is a copolymer of unsaturated carboxylic acid and 01-30 unsaturated alkyl carboxylate, preferably $C_1$-$C_4$. Said copolymer comprises at least one hydrophilic repeat unit of unsaturated olefinic carboxylic acid type and at least one hydrophobic repeat unit of the type ($C_1$-$C_{30}$) alkyl ester of unsaturated carboxylic acid.

Preferably, these copolymers are selected from among those in which the hydrophilic repeat unit of unsaturated olefinic carboxylic acid type corresponds to the monomer of following formula (I):

$$H_2C=\underset{R_1}{\overset{}{C}}-\underset{O}{\overset{\|}{C}}-OH \qquad (I)$$

where: $R_1$ is H or $CH_3$ or $C_2H_5$, i.e. repeat units of acrylic acid, methacrylic acid or ethacrylic acid, and in which the hydrophobic repeat unit of the type ($C_1$-$C_{30}$) alkyl ester of unsaturated carboxylic acid corresponds to the monomer of following formula (II):

$$H_2C=\underset{R_2}{\overset{}{C}}-\underset{O}{\overset{\|}{C}}-OR_3 \qquad (II)$$

where: $R_2$ is H or $CH_3$ or $C_2H_5$ (i.e. acrylate, methacrylate or ethacrylate repeat units) and preferably H (acrylate repeat units) or $CH_3$ (methacrylate repeat units), $R_3$ designating a $C_1$-$C_{30}$ alkyl radical, preferably $C_1$-$C_4$.

Among this type of copolymers, more particular use is made of those formed from a mixture of monomers comprising:
(i) essentially acrylic acid;
(ii) an ester of formula (II) described above and where $R_2$ is H or $CH_3$, $R_3$ is an alkyl radical having 1 to 4 carbon atoms.

(iii) and a crosslinking agent which is a well-known unsaturated polyethylenic copolymerisable monomer such as diallyl phthalate, trimethylolpropane tri(meth)acrylate, diallyl itaconate, diallyl fumarate, diallyl maleate, zinc (meth)acrylate, allyl (meth)acrylate, divinylbenzene, (poly) ethyleneglycol dimethacrylate, methylene-bis-acrylamide, and castor oil.

In one embodiment, the crosslinked polymer or crosslinked copolymer is a polymer or copolymer of acrylic acid and/or methacrylic acid, and/or alkyl acrylate having 1 to 30 carbon atoms, preferably 1 to 4 carbon atoms, and/or alkyl methacrylate having 1 to 30 carbon atoms, preferably 1 to 4 carbon atoms.

In one embodiment, the crosslinked copolymer is a crosslinked copolymer of methacrylic acid and alkyl acrylate having 1 to 4 carbon atoms, preferably 2 carbon atoms.

In the invention, and unless otherwise stated, by «crosslinked copolymer of methacrylic acid an alkyl acrylate having 1 to 4 carbon atoms», it is meant a crosslinked copolymer resulting from polymerisation of a monomer of methacrylic acid and a monomer of alkyl acrylate having 1 to 4 carbon atoms.

Preferably, in this copolymer methacrylic acid represents from 20 to 80 weight %, preferably 35 to 65 weight % of the total weight of the copolymer.

Preferably, in this copolymer, the alkyl acrylate represents from 15 to 80 weight %, preferably 35 to 65 weight % of the total weight of the copolymer.

In particular, the alkyl acrylate is selected from among alkyl methacrylate, ethyl acrylate and butyl acrylate.

In one embodiment, the crosslinked polymer is crosslinked copolymer of the invention contained in the continuous aqueous phase is selected from the group formed by the following polymers or copolymers: Acrylates Copolymer, Acrylates crosspolymer-4, Acrylates crosspolymer-3, Polyacrylate-2 Crosspolymer et Polyacrylate-14 (INCI names).

Among said above polymers, particular preference is given in the present invention to the products sold by LUBRIZOL under the trade names Fixate Superhold (INCI name=Polyacrylate-2 Crosspolymer), Fixate Freestyle Polymer (INCI name=Acrylates crosspolymer-3), Carbopol® Aqua SF1 (INCI name=Acrylates copolymer) and Carbopol® Aqua SF2 (INCI name=Acrylates crosspolymer-4).

Preferably, the crosslinked copolymer is Carbopol® Aqua SF1 (INCI name=Acrylates copolymer).

In one embodiment, the crosslinked copolymer is selected from among crosslinked copolymers of acrylic or methacrylic acid and alkyl acrylates having 1 to 4 carbon atoms.

In the invention, the dispersion of the invention may comprise from 0.1 to 10 weight %, preferably 0.5 to 8 weight % and more preferably 1 to 3 weight % of crosslinked polymer(s) or crosslinked copolymer(s) relative to the total weight of said dispersion.

In the invention, the dispersions of the invention may comprise a carbomer and a crosslinked copolymer Carbopol® Aqua SF1 (INCI name=Acrylates copolymer).

Cationic Polymer

In one embodiment, the droplets and in particular the shell of said droplets also comprise at least one polymer of cationic type. They may also comprise several polymers of cationic type. This cationic polymer is the one mentioned above which forms the shell via coacervation with the anionic polymer.

In the present application, and unless otherwise stated, by "polymer of cationic type" or «cationic polymer» it is meant a polymer comprising chemical functions of cationic type. The term cationic polyelectrolyte can also be used.

Preferably, the cationic polymer is lipophilic or liposoluble.

In the present application, and unless otherwise stated, by "chemical function of cationic type", it is meant a chemical function B capable of capturing a proton to give a $BH^+$ function. Depending on the conditions of the medium in which it is contained, the polymer of cationic type therefore comprises chemical functions in B form or else in $BH^+$ form, its conjugated acid.

As example of chemical functions of cationic type, mention can be made of primary, secondary and tertiary amine functions, optionally present in the form of ammonium cations.

As example of polymer of cationic type, mention can be made of any polymer formed by polymerisation of monomers in which at least one part carries chemical functions of cationic type, such as primary, secondary or tertiary amine functions.

Such monomers are aziridine for example, or any ethylenically unsaturated monomer comprising at least one primary, secondary or tertiary amine function.

Among the examples of cationic polymers suitable for implementing the invention, mention can be made of amodimethicone, derived from a silicone polymer (polydimethylsiloxane, also called dimethicone), modified by primary amine and secondary amine functions.

Mention can also be made of derivatives of amodimethicone e.g. copolymers of amodimethicone, aminopropyl dimethicone, and more generally linear or branched silicone polymers comprising amine functions.

Mention can be made of the copolymer bis-isobutyl PEG-14/amodimethicone, IBis (C13-15 Alkoxy) PG-Amodimethicone, Bis-Cetearyl Amodimethicone and bis-hydroxy/methoxy amodimethicone.

Polymers of polysaccharide type can also be cited comprising amine functions, such as chitosan or derivatives of guar gum (guar hydroxypropyltrimonium chloride).

Polymers of polypeptide type can also be cited comprising amine functions, such as polylysine.

Polymers of polyethyleneimine type can also be cited comprising amine functions, such as linear or branched polyethyleneimine.

In one embodiment, the droplets and in particular the shell of said droplets comprise a cationic polymer which is a silicone polymer modified by a primary, secondary or tertiary amine function, such as amodimethicone.

In one embodiment, the droplets and in particular the shell of said droplets, comprise amodimethicone.

In one particularly preferred embodiment, the cationic polymer meets the following formula:

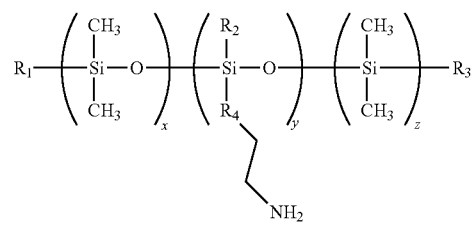

where:
$R_1$, $R_2$ and $R_3$, are each independently OH or $CH_3$;
$R_4$ is a group —$CH_2$— or group —X—NH— where X is C3 or C4 divalent alkylene radical;

x is an integer of between 10 and 5 000, preferably between 30 and 1 000, and better still between 80 and 300;

y is an integer of between 1 and 1 000, preferably between 2 and 1 000, more preferably between 4 and 100, and better still between 5 and 20; and z is an integer of between 0 and 10, preferably between 0 and 1, and better still it is 1.

In the above-mentioned formula, when $R_4$ is a group —X—NH—, X is linked to the silicon atom.

In the above-mentioned formula, $R_1$, $R_2$ and $R_3$ are preferably $CH_3$.

In the above-mentioned formula, $R_4$ is preferably a group —$(CH_2)_3$—NH—.

In the invention, each droplet may comprise from 0.01 to 10 weight %, preferably 0.05 to 5 weight %, of cationic polymer(s) in particular of amodimethicone(s), relative to the total weight of the fatty phase.

In the invention, each droplet may advantageously comprise between 0.5% and 5%, preferably between 1% and 4.5%, in particular between 1.5% and 4%, better still between 2% and 3.5%, and in particular between 2.5% and 3% by weight of cationic polymer(s), in particular of amodimethicone(s), relative to the total weight of the fatty phase. These contents are advantageous since they improve the mechanical strength of the droplets (G1).

Fatty Phase

In the invention, a dispersion comprises a dispersed phase in the form of droplets comprising at least one fatty (or oily) phase, at least one pigment in a content higher than 23.5 weight % relative to the weight of said fatty phase, and optionally at least one cationic polymer such as described previously and/or at least one gelling agent differing from anionic and cationic polymers described above.

Oils

By «oil» it is meant a fat liquid at ambient temperature (25° C.).

As oils that can be used in the composition of the invention, mention can be made for example of:

hydrocarbon oils of vegetable origin such as hydrogenated jojoba oil, hydrogenated sunflower seed oil, hydrogenated castor oil, hydrogenated copra oil;

hydrocarbon oils of animal origin such as perhydrosqualene and squalane;

synthetic esters and ethers, in particular of fatty acids, such as oils of formulas $R_1COOR_2$ and $R_1OR_2$ where $R_1$ is the remainder of a $C_8$ to $C_{29}$ fatty acid, and $R_2$ is a $C_3$ to $C_{30}$ branched or non-branched hydrocarbon chain e.g. PurCellin oil, isononyl isononanoate, isodecyl neopentanoate, isopropyl myristate, ethyl-2-hexyl palmitate, octyl-2-dodecyl stearate, octyl-2-dodecyl erucate, isostearyl isostearate; hydroxylated esters such as isostearyl lactate, octylhydroxystearate, octyldodecyl hydroxystearate, diisostearyl-malate, triisocetyl citrate, heptanoates, octanoates, fatty alcohol decanoates; polyol esters such as propylene glycol, dioctanoate, neopentylglycol diheptanoate and diethyleneglycol diisononanoate; and pentaerythritol esters such as pentaerythrityl tetrabehenate (DUB PTB) or pentaerythrityl tetraisostearate (Prisorine 3631);

linear and branched hydrocarbons, of mineral or synthetic origin, such as paraffin oils whether or not volatile and derivatives thereof, Vaseline, polydecenes, hydrogenated polyisobutene such as Parleam oil;

silicone oils e.g. polydimethylsiloxanes (PDMS) whether or not volatile with linear or cyclic silicone chain, liquid or pasty at ambient temperature, in particular cyclopolydimethylsiloxanes (cyclomethicones) e.g. cyclohexasiloxane and cyclopentasiloxane; polydimethylsiloxanes (or dimethicones) comprising alkyl, alkoxy or phenyl groups either pendant or at the end of the silicone chain, groups having 2 to 24 carbon atoms; phenylated silicones such as phenyltrimethicones, phenyldimethicones, phenyltrimethylsiloxydiphenyl-siloxanes, diphenyl-dimethicones, diphenylmethyldiphenyl trisiloxanes, les 2-phenylethyltrimethyl-siloxysilicates, and polymethylphenylsiloxanes;

fatty alcohols having 8 to 26 carbon atoms, such as cetyl alcohol, stearyl alcohol and mixture thereof (cetostearyl alcohol), or octyldodecanol;

fluorinated oils, partially hydrocarbon- and/or silicone-based such as described in JP-A-2-295912;

and mixtures thereof.

It is within the reach of skilled persons to adjust the type and/or content of oil(s), in particular to ensure satisfactory solubilisation (or homogenisation) of the pigment(s) and of the cationic polymer(s) if provided.

Therefore, the fatty phase advantageously comprises less than 40%, preferably less than 30%, in particular less than 20% and better still less than 10 weight % of hydrocarbon oil(s) of vegetable origin relative to the total weight of the fatty phase.

Advantageously, a dispersion of the invention comprises at least one non-volatile hydrocarbon oil (or oil H1) containing more than 90%, preferably more than 95% of fatty acids having a chain length equal to or greater than 18 carbon atoms, preferably equal to or greater than 20 carbon atoms.

Preferably, more than 90%, more preferably more than 95% of the fatty acids of the non-volatile hydrocarbon oil have a chain length of between $C_{18}$ and $C_{36}$, preferably between $C_{20}$ and $C_{28}$, better still between $C_{20}$ and $C_{22}$.

By «non-volatile» it is meant an oil having nonzero vapour pressure at ambient temperature and atmospheric pressure, which is lower than 0.02 mm Hg (2.66 Pa) and better still lower than 10-3 mm Hg (0.13 Pa).

Therefore as oils H1, mention can be made of jojoba oil, flax oil, *Perilla* oil, *Inca* Inchi oil, rosehip seed oil, rapeseed oil, hemp oil, sweet almond oil, corn oil, apricot oil, castor oil, Meadowfoam oil (INCI: Limnanthes Alba (Meadowfoam) Seed Oil) and mixtures thereof, and preferably jojoba oil and/or Meadowfoam oil, and better still Meadowfoam oil.

The use of oils H1 in particular of Meadowfoam oil in the fatty phase of a dispersions of the invention has advantageous effects in terms of a reduction in opacification of the continuous aqueous phase and/or in adhesion of droplets to packaging walls and/or in aggregation of droplets.

Preferably, a dispersion of the invention and in particular the fatty phase does not comprise a crystallisable oil having a melting point ($T_M$) lower than 100° C.

A dispersion of the invention may comprise from 1% to 76.49%, in particular from 1% to 75.50%, preferably from 5% to 70%, and better still from 10% to 60%, in particular from 20% to 50% by weight of oil(s) relative to the total weight of the fatty phase.

Pigments

The fatty phase of a dispersion of the invention comprises at least one pigment in a content higher than 25 weight % relative to the weight of the fatty phase. The use of several pigments allows grading of the colour of the fatty phase of the droplets and hence of the dispersion, as desired.

By «pigment» it is meant a colouring chemical substance insoluble in the phase in which the pigment is contained. By «insoluble» it is meant that solubility at 20° C. of the pigment in the phase in which the pigment is contained is less than 1 g/L, in particular less than 0.1 g/L, preferably less than 0.001 g/L.

Each pigment can independently be an organic, inorganic or hybrid organic-inorganic pigment. They are typically inorganic pigments.

The colouring imparted by a dispersion of the invention can be measured for example by spectrocolorimetry and/or spectrophotocolorimetry.

Coverage corresponds to the capacity of a composition to «mask the skin»/to «hide imperfections».

The coverage of a composition is measured at a finished thickness of 50 μm for compositions liquid at 25° C. to be applied to the lips, in particular liquid lipsticks, liquid lip shines and liquid lip salves, and at a thickness of 150 μm for eyeshadows, liquid foundations, mascaras and other liquid makeup products not intended to be applied to the lips. The composition is spread over matt black and matt white contrast cards e.g. of the trade name LENETA Form WPI for the matt black card and our Leneta IA for the matt white card. Application can be made using an automatic spreader. If the composition is non-homogeneous e.g. such as dispersion of the invention, in particular when the droplets (G1) are macroscopic, a step to mix said dispersion e.g. on Rayneri mixer prior to the application step (i.e. spreading over the cards) is preferably conducted to achieve homogeneity. Measurements are taken on the compositions thus applied. Reflectance data are acquired with a MINOLTA 3700-d spectrophotometer (diffuse illumination measurement geometry and D65/10° viewing, specular component mode excluded, small opening (CREISS)) against black and white backgrounds. Spectra are expressed in colorimetric coordinates in the CIELab76 colour space as required by Recommendation 15.2004 given by the International Commission on Illumination. The contrast ratio or coverage is calculated by obtaining the arithmetic mean of Y against a black background, divided by the mean value of Y against a white background, multiplied by 100.

As pigments, particular mention can be made of titanium dioxide, zinc dioxide, zirconium or cerium oxides, and iron or chromium oxides, manganese violet, ultramarine blue, hydrated chromium and iron blue, and mixtures thereof. The preferred mineral pigments are iron oxides, in particular red iron oxide, yellow iron oxide, brown iron oxide, black iron oxide, titanium dioxide and mixtures thereof.

The pigment is preferably an iron oxide, in particular red iron oxide, yellow iron oxide, brown iron oxide, black iron oxide and mixtures thereof.

Each pigment can be a non-treated pigment of treated pigment. In the meaning of the application, by «treated pigment» it is meant a pigment that has been treated with an additive to improve the dispersibility thereof within an oily or aqueous composition, in particular one of the additives defined below. By «non-treated pigment» or «untreated pigment», it is meant a pigment that has not been treated with said additive.

In the light of the foregoing, the fatty phase of the droplets of a dispersion of the invention comprises a high content of pigment(s).

Nevertheless, the continuous aqueous phase even the inner aqueous phase for a complex dispersion such as described below, may also comprise at least one pigment.

Preferably, when the phase comprising pigments is a fatty (or oily) phase, said phase also comprises hydroxystearic acid or polyhydroxy stearic acid such as the one marketed by Phoenix Chemical under the trade name PELEMOL PHS-8, preferably in a content of between 0.5% and 10%, in particular between 1.5% and 6%, better still between 2.5% and 4% by weight relative to the total weight of the phase under consideration.

The presence of said particular compound(s) is advantageous in that:
  they allow reducing of the viscosity of a fatty phase comprising at least one pigment, for example pigment/oil grindings (60:40), even more so of a phase with high pigment content, and hence can make the phase fluid and more easily processable in particular for fluidic systems such as described below; and
  they allow maintained droplet size. The inventors have observed that the use of pigment(s) in fatty phase dispersed in a dispersion of the invention generally leads to a reduction in droplet size in comparison with one same dispersion devoid of said pigment(s).

Finally, the maintained integrity of a dispersion of the invention in the presence of these compound(s) is unexpected. In general, these compound(s) destabilise the shell comprising at least one anionic polymer and at least one cationic polymer.

According to a first alternative, the pigment used is a non-treated, non-ground pigment (pigment used «as such»).

According to a second alternative, the pigment used has been subjected to prior treatment to make it more easily dispersible when formulating the pigment i.e. more easily dispersible in the phase under consideration. This prior treatment entails grinding the pigment and/or pre-treating the same with an additive to improve its dispersibility, before formulation thereof in the form of a series of coloured particles.

The use of a ground pigment and/or pre-treated pigment via a dispersibility-improving additive:
  contributes towards low viscosity of a liquid containing a ground and/or pre-treated pigment;
  contributes towards preparing a dispersion having a dispersed fatty phase with very high pigment content comprising more than 23.5%, generally more than 25%, in particular more than 30%, even more than 40% by weight of pigment(s) relative to the weight of the dispersed fatty phase;
  contributes towards reducing, even preventing sedimentation of pigment(s) in the phase(s) in which they are contained; and/or
  contributes towards reducing, even preventing aggregation of pigments in the phase(s) in which they are contained.

In general, when several pigments are used, they all undergo the same treatment i.e. they are all ground and/or they are all pre-treated. It is possible however that some are ground and non-treated, and others are treated and ground or non-ground.

In a first embodiment according to the second alternative, the at least one pigment is pre-treated with an additive to improve the dispersibility of the pigment.

The type of additive improving the dispersibility of the pigment is dependent on the hydrophilic or lipophilic nature of the phase(s) which are to comprise this treated pigment.

If a dispersion uses several pre-treated pigments, these can be pre-treated with the same or different additives.

An additive improving the dispersibility of the pigment within an oily phase is selected for example from among hydrogenated lecithin, a silicone, wax, amino acid or one of the salts thereof, and an amino acid ester or one of the salts thereof, and mixtures hereof. Hydrogenated lecithin comprises phosphate mono- and di-esters having fatty chains which promote dispersibility in an oily phase. The silicone additive can be obtained either from a silicone precursor such as an alkoxyalkylsilane e.g triethoxycaprylsilane, or such as a trialkylsiloxysilicate e.g. trimethylsiloxysilicate, or it may be a silicone such as dimethicone or one of the derivatives thereof e.g. bis-hydroxyethoxypropyl dimethicone, or it can be obtained from a mixture of silicone and one of its precursors e.g. a mixture of dimethicone and trimethylsiloxysilicate. The silicone additive can be a hybrid treatment in particular a mixture of isopropyl titanium triisostearate, bis-hydroxyethoxypropyl dimethicone, PEG-2 soyamine and isophorone diisocyanate (IPDI). The wax for example can be a rose floral wax. The preferred amino acid is cystine, and the preferred amino acid esters are sodium cocoyl glutamate, layroyl arginine or lauroyl lysine.

An additive improving the dispersibility of the pigment in an aqueous phase is selected in particular from among an additive of following formula (I):

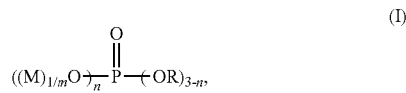

where:
n is 1 or 2;
M is H or a cation;
m is 1 when M is H, and m represents the valence of the cation when M is a cation;
R is:
a group G selected from among a saccharide or group $-[CH_2-CHR_1-O]_q-R_2$ or $-[CH_2-CH(CH_2OH)-O]_q-R_2$ where:
q is an integer of 1 to 1000;
for each $CH_2-CHR_1-O$ unit, $R_1$ is independently H or a methyl;
$R_2$ is H or an alkyl having 1 to 3 carbon atoms; and
a hydrocarbon chain having 1 to 500 carbon atoms substituted by one or more groups: G, phosphate (of formula $OPO_3(M)_{2/m}$) and/or hydroxyl (OH).

The $-[CH_2-CHR_1-O]_q-R_2$ group where $R_1$ is H corresponds to a polyethylene glycol (PEG). The $-[CH_2-CHR_1-O]_q-R_2$ group where $R_1$ is a methyl corresponds to a polypropylene glycol (PPG). The $-[CH_2-CH(CH_2OH)-O]_q-R'$ group corresponds to a polyglycerol.

Typically, q is an integer of 1 to 500, in particular 1 to 100, preferably 1 to 60.

Preferably, n is 2 and the additive has following formula (I'):

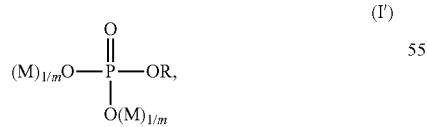

where M, m and R are such as defined above.

In the meaning of the present application, a hydrocarbon chain comprises from 1 to 500 carbon atoms, in particular 1 to 50, typically 1 to 10 carbon atoms, preferably 1 to 5 carbon atoms. The hydrocarbon chains can be linear, branched or cyclic. The preferred hydrocarbon chains are the alkyl groups (preferably having 1 to 10 carbon atoms, in particular 1 to 5 carbon atoms, preferably 1 to 3, such as the methyl, ethyl, n-propyl and isopropyl groups), alkenyl (preferably having 2 to 10 carbon atoms, in particular 2 to 6), aryl (preferably having 6 to 10 carbon atoms), arylalkyl (preferably having 7 to 19 carbon atoms) or alkylaryl (preferably having 7 to 10 carbon atoms). The vinyl group is the preferred alkenyl group. The phenyl group is the preferred aryl group.

A saccharide can be a mono- or polysaccharide. The preferred saccharides are mono- or disaccharide, in particular monosaccharides such as glucose, galactose or fructose.

M can particularly be an inorganic cation such as $Ag^{3+}$, $Al^{3+}$, $Fe^{3+}$, $Fe^{2+}$, $Ag^{2+}$, $Zn^{2+}$, $Sn^{2+}$, $Ca^{2+}$, $Ba^{2+}$, $Ag^+$, $Na^+$ or an organic cation such as a diethanol ammonium (DEA) ($H_3N^+-(CH_2)_2-OH$) or quaternary ammonium.

The following additives of following formulas (II), (III) or (IV) are particularly adapted for implementing the invention:

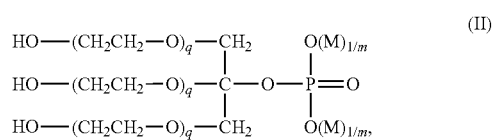

where M, m and q are such as defined above, (which corresponds to an additive of formula (I) where n is 2 and R is an isopropyl hydrocarbon chain in which each of the carbon atoms is substituted by a group G which represents $-[CH_2-CHR_1-O]_q-R_2$ where $R_1$ and $R_2$ are H),

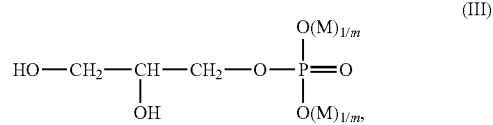

where M and m are such as defined above, (which corresponds to an additive of formula (I) where n is 2, R is a group G of formula $-[CH_2-CH(CH_2OH)-O]_q-R_2$ where q is 1 and $R_2$ is H),

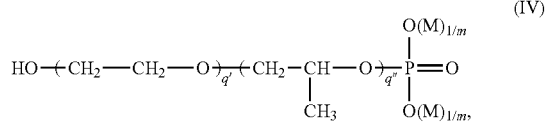

where M and m are such as defined above and q' and q" are each independently an integer of 0 to 1000, generally 0 to 500, in particular 0 to 100, preferably 0 to 60, such that sum of q' and q" independently represents an integer of 1 to 1000, (which corresponds to an additive of formula (I) where n is 2, R is a group G of formula $-[CH_2-CHR_1-O]_q-R_2$ where q is the sum of q' and q" and, for the q" first units, $R_1$ is a methyl and for the q' last units, R is H, and $R_2$ is H).

The following additives of formulas (V) and (VI) are also adapted:

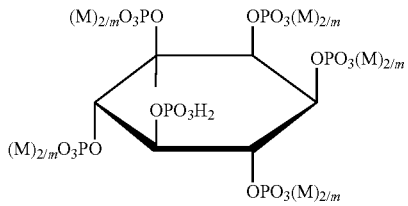

(V)

(which corresponds to an additive of formula (I) where n is 2, R is a cyclohexyl hydrocarbon chain substituted at positions 2, 3, 4, 5 et 6 by a phosphate group of formula $OPO_3H_2$),

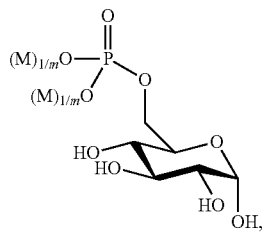

(VI)

(which corresponds to an additive of formula (I) where n is 2, R is a methyl hydrocarbon chain linked to a G glucose group), where M and m are such as defined above.

The following additives are particularly preferred:

glycereth-26 phosphate, of following formula (II'):

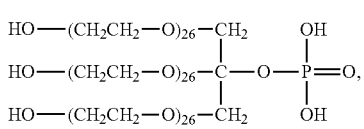

(II')

(which corresponds to an additive of formula (II) where M is H and m is 1), this additive advantageously being commercially available e.g. from Croda®, glycerophosphate, of following formula (III'):

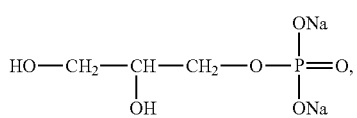

(III')

(which corresponds to an additive of formula (III) where M is Na and m is 1), this additive advantageously being commercially available e.g. from Dr Paul Lohman®, diethanolammonium PEG-26 PPG-30 phosphate of following formula (IV'):

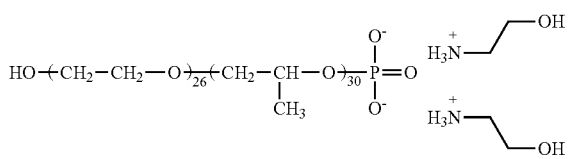

(which corresponds to an additive of formula (IV) where M is a diethanolammonium cation and m is 1), this additive advantageously being commercially available e.g. from Innospec®, phytic acid of following formula (V'):

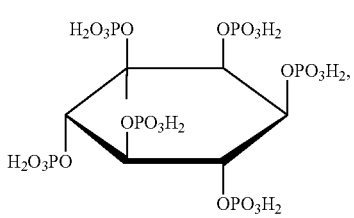

(V')

(which corresponds to an additive of formula (V) where M is H and m is 1), this additive advantageously being commercially available e.g. from Nutriscience®, glucose phosphate of following formula (VI'):

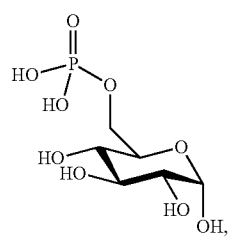

(VI')

(which corresponds to an additive of formula (VI) where M is H and m is 1), this additive advantageously being commercially available.

Advantageously, phytic acid is the additive improving dispersibility of the pigment within an aqueous composition.

A method for preparing a pigment pre-treated with an additive such as defined above is described for example in WO2012/120098.

In this first embodiment of the second alternative using a pre-treated pigment, the pre-treated pigment may or may not subsequently comprise a grinding step. This grinding can limit even remove aggregates of pre-treated pigments, facilitating subsequent incorporation thereof in the phase(s) and/or contributing towards reduced sedimentation of the pigment in the phase(s) in which they are contained.

This grinding step can be performed in the presence or absence (dry grinding) of a binder.

For example, the binder is glycerine, propanediol, a hydrolysate of hydrogenated starch, octyldodecanol, castor oil, mineral oil, isononyl isononanoate, dimethicone and cyclomethicone, isododecane, and mixtures thereof.

Preferably, when the pigment is treated with an additive improving its dispersibility within an oily phase, the binder is selected from among glycerine, octyldodecanol, castor oil, mineral oil, isononyl isononanoate, dimethicone and cyclomethicone, isododecane, and mixtures thereof.

Preferably, when the pigment is not pre-treated or when it is treated with an additive improving its dispersibility within an aqueous phase, the binder is selected from among propanediol, glycerine, a hydrolysate of hydrogenated starch, and mixtures thereof.

The grinding mill is typically selected from among three-cylinder mills, bead mills and plate mills.

If the grinding step is implemented without a binder, the mill can be a pin mill, jet micronizing mill, impact mill, hammer mill, blade mill, ball mill, vibratory mill or cryogenic mill.

In a second embodiment of the second alternative, the at least one pigment is not pre-treated with an additive improving the dispersibility thereof, and the method then comprises a step to grind the pigment. This grinding allows the limiting and even removal of aggregates of pre-treated pigments, facilitating the subsequent incorporation thereof in the phase(s) and/or contributing towards reducing sedimentation of the pigment in the phase(s) in which they are contained.

The embodiments described above for grinding evidently apply (type of grinder, with or without binder).

Advantageously, a dispersion of the invention comprises between 24% and 60%, in particular between 25% and 60%, preferably between 30% and 55%, in particular between 35% and 50%, better still between 40% and 45% by weight of pigment(s) relative to the total weight of the fatty phase (i.e. droplets (G1).

Advantageously, when a phase other than the fatty phase (i.e. droplets G1) also comprises at least one pigment, in particular the continuous aqueous phase, a dispersion of the invention comprises between 0% and 60%, preferably between 5% and 55%, in particular between 10% and 50%, better still between 15 and 40% by weight of pigment(s) relative to the total weight of said phase.

Gelling Agents

The fatty phase of a dispersion of the invention can also comprise at least one gelling agent. Said gelling agent differs from the anionic and cationic polymers, oils and pigments described above. This gelling agent in particular allows adapting of viscosity and/or reduced, even prevented sedimentation of the pigment(s) at ambient temperature and atmospheric pressure.

In the invention, by «gelling agent», it is meant an agent which at ambient temperature and atmospheric pressure allows an increase in the viscosity of the phase(s) in which it is contained, compared with the same phase(s) not containing said gelling agent, and for example reaching a final viscosity of the phase(s) higher than 2 000 mPa·s, preferably higher than 4 000 mPa·s, better still higher than 10 000 mPa·s, and most preferably higher than 100 000 mPa·s.

Preferably, the viscosity of a phase in the presence of said gelling agent is between 2 000 and 100 000 000 mPa·s, more preferably between 4 000 and 1 000 000 mPa·s, and better still between 10 000 and 500 000 mPa·s, at 25° C.

The choice of gelling agent(s) is made having regard to the type of the phase under consideration. For reasons of compatibility with the fatty phase, the gelling agent is lipophilic.

By «lipophilic gelling agent», it is meant a liposoluble or lipodispersible compound capable of gelling the fatty (or oily phase) of a dispersion of the invention.

In one particular embodiment, the gelling agent is heat-sensitive. The expression «heat-sensitive gelling agent» designates an agent able to increase the viscosity of the fatty phase in which it is contained compared to when it does not contain said agent, this viscosity changing reversibly as a function of temperature.

In one embodiment, the gelling agent is selected from among organic or mineral, polymeric or molecular lipophilic gelling agents; fats that are solid at ambient temperature and pressure, selected in particular from among waxes, pasty fats, butters; and mixtures thereof.

Lipophilic Gelling Agent(s)

The gelling agents able to be used in the invention can be organic or mineral, polymeric or molecular lipophilic gelling agents.

As mineral lipophilic gelling agent, optionally modified clays can be cited such as hectorites modified by $C_{10}$ to $C_{22}$ ammonium chloride, hectorite modified by distearyl dimethyl ammonium chloride e.g. the one marketed under the trade name Bentone 38V® by ELEMENTIS. Mention can also be made of hectorite modified by distearyl dimethyl ammonium chloride also known as quaternium-18 bentonite, such as the products marketed or manufactured under the trade names Bentone 34 by Rheox, Claytone XL, Claytone 34 and Claytone 40 marketed or manufactured by Southern Clay, modified clays known under the names benzalkonium and quaternium-18 bentonites marketed or manufactured under the trade names Claytone HT, Claytone GR and Claytone PS by Southern Clay, clays modified by stearyldimethylbenzoylammonium chloride known as steralkonium bentonites, such as the products marketed or manufactured under the trade names Claytone APA and Claytone AF by Southern Clay, and Baragel 24 marketed or manufactured by Rheox.

Mention can also be made of pyrogenated silica optionally with hydrophobic surface treatment and having a particle size of less than 1 μm. It is possible chemically to modify the surface of silica via chemical reaction generating a reduction in the number of silanol groups on the silica surface. It is possible in particular to substitute the silanol groups by hydrophobic groups, to give hydrophobic silica.

The hydrophobic groups can be:

trimethylsiloxyl groups, notably obtained by treating pyrogenated silica in the presence of hexamethyldisilazane. Silicas thus treated are called «Silica silylate» according to CTFA ($8^{th}$ Edition, 2000). They are marketed for example under references Aerosil R812® by DEGUSSA, CAB-O-SIL TS-530® by CABOT; or dimethylsilyloxyl or polydimethylsiloxane groups, obtained in particular via treatment of pyrogenated silica in the presence of polydimethylsiloxane or dimethyldichlorosilane. Silicas thus treated are called «Silica dimethyl silylate» in accordance with CTFA terminology ($8^{th}$ Edition, 2000). They are marketed for example under the references Aerosil R972® and Aerosil R974® by DEGUSSA, CAB-O-SIL TS-610® and CAB-O-SIL TS-720® by CABOT.

Hydrophobic pyrogenated silica particularly has a particle size which can be nanometric to micrometric e.g. in the range of about 5 to 200 nm.

Polymeric organic lipophilic gelling agents are for example elastomeric organopolysiloxanes partly or fully crosslinked and of three-dimensional structure such as those marketed under the trade names KSG6®, KSG16® and KSG18® by SHIN-ETSU, Trefil E-505C® and Trefil E-506C® by DOW-CORNING, Gransil SR-CYC®, SR DMF10®, SR-DC556®, SR 5CYC Gel®, SR DMF 10 Gel® and SR DC 556 Gel® by GRANT INDUSTRIES, SF 1204® and JK 113® by GENERAL ELECTRIC; ethylcellulose such as the one sold under the trade name Ethocel® by DOW CHEMICAL; galactomannans comprising one to six and in particular two to four hydroxyl groups per monosaccharide unit substituted by a saturated or unsaturated alkyl chain, such as guar gum alkylated by $C_1$ to $C_6$ alkyl chains, in particular $C_1$ to $C_3$, and mixtures thereof. Block copolymers of «diblock», «triblock» or «radial» type of polystyrene/polyisoprene, polystyrene/polybutadiene type such as those marketed under the trade name Luvitol HSB® by BASF, of polystyrene/copoly(ethylene-propylene) type such as those marketed under the trade name Kraton® by SHELL CHEMICAL CO or of polystyrene/copoly(ethylenebutylene), type, mixtures of triblock and radial (star) copolymers in isododecane such as those marketed by PENRECO under the trade name Versagel® e.g. the mixture of the triblock copolymer butylene/ethylene/styrene and star copolymer ethylene/propylene/styrene in isododecane (Versagel M 5960).

In one embodiment, the gelling agents able to be used in the invention can be selected from the group formed by polyacrylates; esters of sugar/polysaccharide and fatty acid(s) in particular esters of dextrin and fatty acid(s), esters of glycerol and fatty acid(s) or esters of inulin and fatty acid(s); polyamides, and mixtures thereof.

As lipophilic gelling agent, mention can also be made of polymers having a weight average molecular weight lower than 100 000, comprising a) a polymeric backbone having hydrocarbon repeat units provided with at least one heteroatom, and optionally b) at least one pendant fatty chain and/or at least one terminal fatty chain, optimally functionalized, having 6 to 120 carbon atoms and being linked to these hydrocarbon repeat units such as described in applications WO 02/056847, WO 02/47619, in particular polyamide resins (particularly those comprising alkyl groups having 12 to 22 carbon atoms) such as described in U.S. Pat. No. 5,783,657.

As example of polyamide resin able to be used in the present invention, mention can be made of UNICLEAR 100 VG® marketed by ARIZONA CHEMICAL.

It is also possible to use silicone polyamides of polyorganosiloxane type such as those described in U.S. Pat. Nos. 5,874,069, 5,919,441, 6,051,216 and 5,981,680.

These silicone polymers can belong to the two following families:
 polyorganosiloxanes comprising a least two groups capable of setting up hydrogen interactions, these two groups being positioned in the polymer chain, and/or
 polyorganosiloxanes comprising at least wo groups capable of setting up hydrogen interactions, these two groups being positioned on grafts or branches.

Among the lipophilic gelling agents able to be used in the present invention, further mention can be made of the esters of dextrin and fatty acid such as dextrin palmitates.

In one embodiment, the ester of dextrin and fatty acid(s) of the invention is a mono- or poly-ester of dextrin and at least one fatty acid meeting following formula (II):

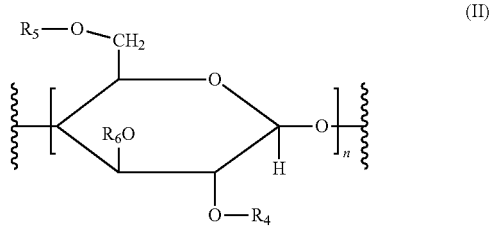

(II)

where:
 n is an integer ranging from 2 to 200, preferably ranging from 20 to 150, in particular ranging from 25 to 50;
 the radicals $R_4$, $R_5$ and $R_6$, the same or different are selected from among hydrogen or an acyl —$COR_a$ group where the radical $R_a$ is a saturated or unsaturated, linear or branched hydrocarbon radical having 5 to 50, preferably 5 to 25 carbon atoms,
 provided that at least one of said radicals $R_4$, $R_5$ or $R_6$ differs from hydrogen.

In one embodiment, $R_4$, $R_5$ and $R_6$ are each independently H or an acyl —$COR_a$ group where $R_a$ is a hydrocarbon radical such as previously defined, provided that at least two of said radicals $R_4$, $R_5$ or $R_6$ are the same and differ from hydrogen.

In one embodiment, when the radicals $R_4$, $R_5$ and $R_6$, the same or different, are a —$COR_a$ radical, they can be selected from among the following radicals: caprylyl, caproyl, lauroyl, myristyl, palmityl, stearyl, eicosanyl, docosanoyl, isovaleryl, ethyl-2 butyryl, ethylmethylacetyl, isoheptanyl, ethyl-2 hexanyl, isononanyl, isodecanyl, isotridecanyl, isomyristyl, isopalmityl, isostearyl, isohexanyl, decenyl, dodecenyl, tetradecenyl, myristyl, hexadecenoyl, palmitoleyl, oleyl, elaidyl, eicosenyl, sorbyl, linoleyl, linolenyl, punicyl, arachidonyl, stearolyl; and mixtures thereof.

Among the esters of dextrin and fatty acid(s) mention can be made for example of dextrin palmitates, dextrin myristates, dextrin palmitates/ethylhexanoates and mixtures thereof.

Particular mention can be made of the esters of dextrin and fatty acid(s) marketed under the trade names Rheopearl® KL2 (INCI name: dextrin palmitate), Rheopearl® TT2 (INCI name: dextrin palmitate ethylhexanoate), and Rheopearl® MKL2 (INCI name: dextrin myristate) by Miyoshi Europe.

Particular mention can be made of the esters of inulin and fatty acid(s) marketed under the trade names Rheopearl® ISK2 r Rheopearl® ISL2 (INCI name: Stearoyl Inulin) by Miyoshi Europe.

In one embodiment, the gelling agent is selected from among polyacrylates resulting from the polymerisation of $C_{10}$-$C_{30}$ alkyl acrylates(s), preferably $C_{14}$-$C_{24}$ alkyl acrylate(s), and more preferably $C_{18}$-$C_{22}$ alkyl acrylate(s).

In one embodiment, the polyacrylates are polymers of acrylic acid esterified with a fatty alcohol in which the saturated carbon chain comprises 10 to 30 carbon atoms, preferably 14 to 24 carbon atoms, or a mixture of said fatty alcohols. Preferably, the fatty alcohol has 18 carbon atoms or 22 carbon atoms.

Among the polyacrylates, more particular mention can be made of stearyl polyacrylate, behenyl polyacrylate. Preferably, the gelling agent is stearyl polyacrylate or behenyl polyacrylate.

Particular mention is made of the polyacrylates marketed under the trade names Interlimer® (INCI name: Poly $C_{10}$-$C_{30}$ alkyl acrylate), in particular Interlimer® 13.1 and Interlimer® 13.6, by Airproducts.

In one embodiment, the gelling agent is an ester of glycerol and fatty acid(s), in particular a mono-, di- or triester of glycerol and fatty acid(s). Typically, said ester of glycerol and fatty acid(s) ca be used alone or in a mixture.

In the invention, it can be an ester of glycerol and a fatty acid, or an ester of glycerol and a mixture of fatty acids.

In one embodiment, the fatty acid is selected from the group formed by behenic acid, isooctadecanoic acid, stearic acid, eicosanoic acid, and mixtures thereof.

In one embodiment, the ester of glycerol and fatty acid(s) has the following formula (III):

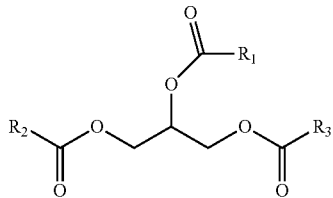

(III)

where: $R_1$, $R_2$ and $R_3$ are each independently selected from among H and a saturated alkyl chain having 4 to 30 carbon atoms, at least one from among $R_1$, $R_2$ and $R_3$ differing from H.

In one embodiment, $R_1$, $R_2$ and $R_3$ are different.

In one embodiment, $R_1$, $R_2$ and/or $R_3$ are a saturated alkyl chain having 4 to 30, preferably 12 to 22, more preferably 18 to 22 carbon atoms.

In one embodiment, the ester of glycerol and fatty acid(s) corresponds to a compound of formula (III) where $R_1$=H, $R_2$=$C_{21}H_{43}$ and $R_3$=$C_{19}H_{40}$.

In one embodiment, the ester of glycerol and fatty acid(s) corresponds to a compound of formula (III) where $R_1$=$R_2$=$R_3$=$C_{21}H_{43}$.

In one embodiment, the ester of glycerol and fatty acid(s) corresponds to a compound of formula (III) where $R_1$=$R_2$=H, and $R_3$=$C_{19}H_{40}$.

In one embodiment, the ester of glycerol and fatty acid(s) corresponds to a compound of formula (III) where $R_1$=$R_2$=H, and $R_3$=$C_{17}H_{35}$.

Particular mention can be made of the esters of glycerol and fatty acid(s) marketed under the trade names Nomcort HK-G (NCI name: Glyceryl behenate/eicosadioate) and Nomcort SG (INCI name: Glyceryl tribehenate, isostearate, eicosadioate), by Nisshin Oillio.

Waxe(s)

By «wax», in the meaning of the invention it is meant a lipophilic compound solid at ambient temperature (25° C.), with reversible solid/liquid state change, having a melting point equal to or higher than 30° C. and possibly of up to 120° C.

The protocol for measuring this melting point is described below.

The waxes able to be used in a composition of the invention can be selected from among solid waxes whether or not deformable at ambient temperature of animal, vegetable, mineral or synthetic origin, and mixtures thereof.

Particular use can be made of hydrocarbon waxes such as beeswax, lanolin wax, Chinese insect wax, rice bran wax, Carnauba wax, Candelilla wax, Ouricurry wax, Alfa wax, cork fibre wax, sugar cane wax, Japan wax and sumac wax; montan wax, microcrystalline waxes, paraffins and ozokerite; polyethylene waxes, waxes obtained by Fisher-Tropsch synthesis, waxy copolymers and the esters thereof.

Particular mention can be made of the waxes marketed under the trade names Kahlwax®2039 (INCI name: Candelilla *cera*) and Kahlwax®6607 (INCI name: *Helianthus annuus* Seed Wax) by Kahl Wachsraffinerie, Casid HSA (INCI name: Hydroxystearic Acid) by SACI CFPA, Performa®260 (INCI name: Synthetic wax) and Performa®103 (INCI name: Synthetic wax) by New Phase, and AJK-CE2046 (INCI name: Cetearyl alcohol, dibutyl lauroyl glutamide, dibutyl ethylhaxanoyl glutamide) by Kokyu Alcohol Kogyo.

Mention can also be made of the waxes obtained by catalytic hydrogenation of animal or vegetable oils having linear or branched $C_8$-$C_{32}$ fatty chains.

Among these, particular mention is made of hydrogenated jojoba oil, hydrogenated sunflower seed oil. hydrogenated castor oil, hydrogenated copra oil and hydrogenated lanolin oil; di-(trimethylol-1,1,1 propane) tetrastearate sold under the trade name «HEST 2T-4S» by HETERENE, di-(trimethylol-1,1,1 propane) tetrabehenate sold under the trade name HEST 2T-4B by HETERENE.

It is also possible to use waxes obtained by transesterification and hydrogenation of vegetable oils, such as castor or olive oil, e.g. the waxes sold under the trade names Phytowax ricin 16L64® and 22L73® et Phytowax Olive 18L57 by SOPHIM. Said waxes are described in application FR2792190.

It is also possible to use silicone waxes which can advantageously be substituted polysiloxanes, preferably with low melting point.

Among commercial silicone waxes of this type, particular mention can be made of those sold under the trade names Abilwax 9800, 9801 or 9810 (GOLDSCHMIDT), KF910 and KF7002 (SHIN ETSU), or 176-1118-3 and 176-11481 (GENERAL ELECTRIC).

The silicone waxes that can be used can also be alkyl or alkoxydimethicones such as the following commercial products: Abilwax 2428, 2434 and 2440 (GOLDSCHMIDT), or VP 1622 and VP 1621 (WACKER), as well as ($C_{20}$-$C_{60}$) alkyldimethicones, in particular ($C_{30}$-$C_{45}$) alkyldimethicones such as the silicone wax sold under the trade name SF-1642 by GE-Bayer Silicones.

It is also possible to use hydrocarbon waxes modified by silicone or fluorine groups e.g.: siliconyl candelilla, siliconyl beeswax and Fluorobeeswax by Koster Keunen.

The waxes can also be selected from among fluorinated waxes.

Butter(s) or Pasty Fats

By «butter» (also called «pasty fat») in the meaning of the present invention, it is meant a lipophilic fatty compound with reversible solid/liquid state change and which, at a temperature of 25° C. and at atmospheric pressure (760 mm Hg), has a liquid fraction and a solid fraction. In other words, the onset melting temperature of the pasty compound can be lower than 25° C. The liquid fraction of the pasty compound measured at 25° C. can represent from 9 to 97 weight % of the compound. This liquid fraction at 25° C. preferably represents between 15 and 85%, more preferably between 40 and 85 weight %. Preferably, the butter(s) have an end melting point lower than 60° C. Preferably, the butter(s) have hardness equal to or lower than 6 Mpa.

Preferably, the butter(s) or pasty fats in the solid state have anisotropic crystalline organisation visible under X-ray observation.

In the meaning of the invention, the melting point corresponds to the temperature of the most endothermic peak observed under differential scanning calorimetry (DSC) such as described in standard ISO 11357-3; 1999. The melting point of a paste or wax can be measured using differential scanning calorimetry (DSC), for example using the calorimeter sold under the trade name "DSC Q2000" by TA Instruments.

Regarding measurement of the melting temperature and determination of the end melting point, the protocols for preparing samples are measurements are such as described in WO2017046305.

The liquid fraction by weight of the butter (or pasty fat) at 25° C. is equal to the ratio between the enthalpy of fusion consumed at 25° C. and the enthalpy of fusion of the butter. The enthalpy of fusion of the butter or pasty compound is the enthalpy consumed by the compound to change from the solid state to the liquid state.

Butter is said to be in the solid state when the entirety of its mass is in solid crystalline form. Butter is said to be in the liquid state when the entirety of its mass is in liquid form. The enthalpy of fusion of butter is equal to the integral of the whole fusion curve obtained with the above-mentioned calorimeter, with a temperature rise of 5° C. or 10° C. per minute, in accordance with standard ISO 11357-3:1999. The enthalpy of fusion of butter is the amount of energy required for the compound to change from the solid state to the liquid state. It is expressed in J/g.

The enthalpy of fusion consumed at 25° C. is the amount of energy absorbed by the sample to change from solid state to the state it exhibits at 25° C. formed of a liquid fraction and a solid fraction. The liquid fraction of butter measured at 32° C. preferably represents from 30 to 100 weight % of the compound, preferably from 50 to 100%, more preferably from 60 to 100 weight % of the compound. When the liquid fraction of butter measured at 32° C. is equal to 100%, the temperature at the end of the fusion range of the pasty compound is equal to or lower than 32° C. The liquid fraction of butter measured at 32° C. is equal to the ratio between the enthalpy of fusion consumed at 32° C. and the enthalpy of fusion of the butter. The enthalpy of fusion consumed at 32° C. is calculated in similar manner as the enthalpy of fusion consumed at 23° C.

For measurement of hardness, the protocols for sample preparation and measurement are such as described in WO2017046305.

The pasty fat or butter can be selected from among synthetic compounds and compounds of vegetable origin A pasty fat can be obtained via synthesis from starting products of vegetable origin.

The pasty fat is advantageously selected from among:
lanoline and derivatives thereof such as lanoline alcohol, oxyethylenated lanolines, acetylated lanoline, esters of lanoline such as isopropyl lanolate, oxypropylenated lanolines;
polymer or non-polymer silicone compounds such as polydimethysiloxanes of high molecular weight, polydimethysiloxanes with side chains of alkyl or alkoxy type having 8 to 24 carbon atoms, in particular stearyl dimethicones,
polymer or non-polymer fluorinated compounds;
vinyl polymers, in particular
homopolymers of olefins,
copolymers of olefins,
homopolymers and copolymers of hydrogenated dienes;
linear and branched oligomers, homo or copolymers of alkyl (meth)acrylates preferably having a $C_8$-$C_{30}$ alkyl group;
homo and copolymer oligomers of vinyl esters having $C_8$-$C_{30}$, alkyl groups;
homo and copolymer oligomers of vinylethers having $C_8$-$C_{30}$ alkyl groups;
liposoluble polyethers resulting from polyetherification between one or more $C_2$-$C_{100}$ diols, preferably $C_2$-$C_{50}$, esters and polyesters; and
mixtures thereof.

In one preferred embodiment of the invention, the particular butter(s) are of vegetable origin such as those described in Ullmann's Encyclopedia of Industrial Chemistry («Fats and Fatty Oils», A. Thomas, published on 15 Jun. 2000, D01: 10.1002/14356007.a10_173, item 13.2.2.2. Shea Butter, Borneo Tallow, and Related Fats (Vegetable Butters)).

More particular mention can be made of C10-C18 triglycerides (INCI name: C10-C18 Triglycerides) which at a temperature of 25° C. and at atmospheric pressure (760 mm Hg) comprise a liquid fraction and a solid fraction, shea butter, *nilotica* shea butter (*Butyrospermum parkii*), Galam butter, (*Butyrospermum parkii*), borneo butter or fat, or tengkawang tallow) (*Shorea stenoptera*), *Shorea* butter, Illipe butter, *Madhuca* or *Bassia Madhuca longifolia* butter, mowrah butter (*Madhuca Latifolia*), Katiau butter (*Madhuca mottleyana*), Phulwara butter (*M. butyracea*), mango butter (*Mangifera indica*), murumuru butter (*Astrocatyum murumuru*), Kokum butter (*Garcinia Indica*), Ucuuba butter (*Virola sebifera*), tucuma butter, Painya butter (Kpangnan) (*Pentadesma butyracea*), coffee butter (*Coffea arabica*), apricot butter (*Prunus armeniaca*), Macadamia butter (*Macadamia Temifolia*), grapeseed butter (*Vitis vinifera*), avocado butter (*Persea gratissima*), olive butter (*Olea europaea*), sweet almond butter (*Prunus amygdalus dulcis*), cocoa butter (*Theobroma cacao*) and sunflower seed butter, butter having the INCI name *Astrocaryum murumuru* Seed Butter, butter having the INCI name *Theobroma grandiflorum* Seed Butter, and butter having the INCI name *Irvingia gabonensis* Kernel Butter, the esters of jojoba (mixture of wax and hydrogenated jojoba oil) (INCI name: Jojoba esters) and the ethyl esters of shea butter (INCI name: Shea butter ethyl esters), and mixtures thereof.

Among the gelling agents of the invention mention can also be made of THIXCIN® R by Elementis Specialties (INCI name: Trihydroxystearin) or Estogel by PolymerExpert (INCI: Castor oil/IPDI Copolymer, Caprylic/Capric triglyceride).

Preferably, the gelling agent is selected from among mineral lipophilic gelling agents such as optionally modified clays.

A gelling agent of a dispersed fatty phase of the invention can be a heat-sensitive gelling agent, namely which reacts to heat and in particular a gelling agent solid and ambient temperature and liquid at a temperature higher than 40° C., preferably higher than 50° C.

Advantageously, a gelling agent of a fatty phase of the invention is a thixotropic gelling agent capable of imparting thixotropic behaviour to the solution in which it is contained. Said thixotropic gelling agent is selected in particular from among pyrogenated silicas optionally having hydrophobic treatment as described in the foregoing.

In the invention, a dispersion of the invention may comprise from 0.5 to 70%, preferably 1 to 76%, in particular 1.5 to 50%, better still 2 to 40%, in particular 5 to 30%, and preferably from 10 to 20% by weight of gelling agent(s) relative to the total weight of the fatty phase.

Additional Compound(s)

In the invention, the continuous aqueous phase and/or fatty phase of a dispersion of the invention can further comprise at least one additional compound differing from the above-mentioned anionic and cationic polymers, oils, pigments and gelling agents.

Fillers with Line-Blurring Effect/«Soft-Focus» Effect Fillers

The continuous aqueous phase and/or dispersed fatty phase, in particular the dispersed fatty phase, of a dispersion of the invention may also comprise at least one substance having a line-blurring effect.

A substance having a line-blurring effect is able to modify and/or mask wrinkles through its intrinsic physical properties. In particular these substances can modify wrinkles through a tautening effect, camouflage effect, or blurring effect.

As compounds having line-blurring effect, the following examples can be given:
- porous silica microparticles e.g. Silica Beads® SB 150 and SB 700 by Miyoshi of mean size de 5 µm, and SUNSPHERES® H series by Asahi Glass e.g. H33, H51 of respective sizes 3.5 and 5 µm, and Sensibead Si 175 and Sensibead Si 320 by Sensient Cosmetic Technologies of respective sizes 7 µm and 5 µm;
- hollow hemispherical particles of silicone resins such as NLK 500®, NLK 506® and NLK 510® by Takemoto Oil and Fat, described in particular in EP 1 579 849;
- silicone resin powders e.g. SILICON Resin Tospearl® 145 A DE GE silicone of mean size 4.5 µm;
- acrylic copolymer powders in particular of poly(methyl methacrylate) e.g. PMMA Jurimer MBI® particles by Nihon Junyoki of mean size 8 µm, hollow PMMA spheres sold under the trade name COVABEAD® LH 85 by Sensient Cosmetic Technologies, and expanded microspheres of vinylidene/acrylonitrile/methylene methacrylate sold under the trade name Expancel®;
- wax powders such as Paraffin wax Microloase® 114S particles by Micropowders of mean size 7 µm;
- polyethylene powders comprising at least one ethylene/acrylic acid copolymer e.g. FLOBEADS® EA 209 E by Sumimoto of mean size 10 µm;
- powders of crosslinked, elastomeric organopolysiloxanes coated with silicone resin in particular silsesquioxane under the trade name KSP 100®, KSP 101®, KSP 102®, KSP 103®, KSP 104® and KSP 105® by Shin Etsu;
- composite powders of talc/dioxide or titanium/aluminium oxide/silica e.g. Coverleaf AR 80® by Catalyst & Chemical;
- talc, mica, kaolin, lauryl glycine, starch powders crosslinked by octenyl succinic anhydride, boron nitride, polytetrafluoroethylene powders, precipitated calcium carbonate, magnesium hydrogen carbonate, barium sulfate, hydroxyapatite, calcium silicate, cerium dioxide and glass or ceramic microcapsules;
- synthetic or natural, mineral or organic, hydrophilic or hydrophobic fibres such as fibres of silk, cotton, wool, linen, cellulose extracted from wood, vegetables or algae in particular, polyamide (Nylon®), modified cellulose, poly-p-phenylene terephthalamide, acrylic, polyolefin, glass, silica, aramid, carbon, polytetrafluoroethylene (Teflon®), insoluble collagen, polyesters, vinyl or vinylidene polychloride, polyvinyl alcohol, polyacrylonitrile, chitosan, polyurethane, polyethylene phthalate, fibres formed of a mixture of polymers, resorbable synthetic fibres and the mixtures thereof described in patent application EP 1 151 742;
- crosslinked elastomeric spherical silicones such as Trefil E-505C® or E-506 C® by Dow Corning;
- abrasive fillers which via mechanical effect provide smoothing of skin microrelief, such as abrasive silica e.g. Abrasif SP® by Semanez, or nut or nutshell powders (apricot, walnut e.g. by Cosmetochem); and mixtures thereof.

Fillers having an effect on signs of ageing are selected in particular from among porous silica microparticles, hollow hemispherical particles of silicones, silicone resin powders, acrylic copolymer powders, polyethylene powders, crosslinked elastomeric organopolysiloxanes powders coated with silicone resin, composite powders of talc/dioxide or titanium/aluminium oxide/silica, precipitated calcium carbonate, magnesium hydrogen carbonate, barium sulfate, hydroxyapatite, calcium silicate, cerium dioxide and glass or ceramic microcapsules, silk fibres, cotton fibres and mixtures thereof.

Colouring Agent

The continuous phase and/or dispersed phase, in particular the fatty phase, can also comprise at least one colouring agent differing from the above-mentioned pigment(s) and fillers.

A colouring agent can be selected in particular from among colouring agents whether or not water-soluble, whether or not liposoluble, organic or inorganic, materials with optical effect, liquid crystals and mixtures thereof.

In particular, a colouring agent can be a colouring agent and/or nacre e.g. Covapearl Star dore 2375 by Sensient Cosmetic Technologies or Covapearl antique Silver 239 by Sensient Cosmetic Technologies. Preferably a colouring agent or nacre is chosen differing from the pigment used. By «colouring agent» it is meant a colouring chemical substance soluble in the coloured particle (or phase of the coloured particle in which the colouring agent is contained). By «soluble» it is meant that the solubility at 20° C. of the colouring agent in the coloured particle is greater than 2 g/L, in particular greater than 5 g/L, preferably greater than 10 g/L.

Preferably, when the dispersion of the invention is multiphase, the phase comprising the pigment(s) differs from the phase comprising said nacre(s) and/or colouring agent(s). An enhanced, even unexpected, visual effect is obtained for users who, in one particular embodiment, see a product leaving its container that has a colour (that of the pigment(s) of the dispersed fatty phase) differing from the expected colour (that of the nacre(s) and/or colouring agent(s).

Additionally, the continuous phase and/or dispersed phase in particular the fatty phase of a dispersion of the invention can further comprise powders; glitter; reflective particles (i.e. particles having a size, structure, in particular thickness of constituent layers, physical and chemical nature, surface condition enabling them to reflect incident light). This reflection can optionally have sufficient intensity so that on the surface of the dispersion or composition of the invention, when applied to the substrate to be made up, it creates highlight points visible to the naked eye i.e. points that are more luminous contrasting with the environment from which they shine forth); particulate agents insoluble in the fatty phase; elastomers of emulsifying and/or non-emulsifying silicones in particular such as described in EP2353577; preserving agents; humectants; stabilisers; chelating agents; film-forming polymers (i.e. polymers capable, alone or in the presence of an auxiliary film-forming agent, of forming a continuous film adhering to a substrate in particular onto keratin material and in particular the skin); auxiliary film-forming agents such as aforementioned; emollients; modifying agents selected from among texturing agents, viscosifying agents (e.g. aqueous phase gelling/texturizing agents differing from the above-mentioned base); pH modifiers, osmotic strength modifiers and/or modifiers of refractive index etc. . . . or any usual cosmetic additive; and mixtures thereof.

In one embodiment, the particulate agents insoluble in the fatty droplet phase are selected from the group formed by ceramics, polymers, in particular acrylic polymers and mixtures thereof.

Texturizing Agents

Depending on the fluidity of the dispersion it is desired to obtain, it is possible to incorporate in the dispersion of the invention, in particular in the continuous aqueous phase, one or more texturizing agents.

As hydrophilic texturizing agents i.e. soluble or dispersible in water and therefore able to be contained in the aqueous phase of a dispersion of the invention, mention can be made of:
- natural texturizing agents selected in particular from among algae extracts, plant exudates, seed extracts, microorganism exudates such as alcasealan (INCI: Alcaligenes Polysaccharides), and other natural agents in particular hyaluronic acid;
- semi-synthetic texturizing agents selected in particular from among cellulose derivatives and modified starches;
- synthetic texturizing agents selected in particular from among homopolymers of (meth)acrylic acid or one of the esters thereof, copolymers of (meth)acrylic acid or one of the esters thereof, copolymers of AMPS (2-acrylamido-2-methylpropane sulfonic acid), associative polymers;
- other texturizing agents selected in particular from among polyethylene glycols (marketed under the trade name Carbowax), clays, silicas such as those marketed under the trade names Aerosil® 90/130/150/200/300/380), glycerine; and
- mixtures thereof.

By «associative polymer» in the meaning of the invention it is meant an amphiphilic polymer having in its structure at least one fatty chain and at least one hydrophilic portion; associative polymers conforming to the present invention can be anionic, cationic, non-ionic or amphoteric; in particular they are such as described in FR 2 999 921.

These hydrophilic texturizing agents are described in more detail in FR3041251.

These hydrophilic texturizing agents can also reinforce the kinetic stability of a dispersion of the invention, in particular when the continuous aqueous phase is liquid at ambient temperature and atmospheric pressure.

The continuous phase and/or dispersed phase, in particular the fatty phase, of a dispersion of the invention can also comprise at least one active substance, notably biological or cosmetic, preferably selected from among hydrating agents, healing agents, depigmenting agents, UV filters, peeling agents, antioxidants, active substances stimulating the synthesis of dermal and/or epidermal macromolecules, dermorelaxants, antiperspirant agents, soothing agents, anti-ageing agents, fragrances and mixtures thereof.

Preferably a dispersion of the invention also comprises UV filters in particular such as described in FR3041251.

Evidently, those skilled in the art will take care to choose additional compound(s) and or active substance(s) mentioned above and/or their respective amounts so that the advantageous properties of a dispersion of the invention are not or not substantially affected by the envisaged addition. In particular, the type and/or amount of the additional compound(s) and/or active substance(s) are dependent on the aqueous or oily nature of the phase under consideration and/or on the method used (in particular of «non-microfluidic» or «microfluidic» type). These adjustments lie within the reach of skilled persons.

In one embodiment, the dispersions of the invention may also comprise at least one polyol. The term "polyol" designates a compound having more than one hydroxyl group (—OH). All polyols desirably used in cosmetic or dermatological compositions can be used in the present invention. Examples of polyols can comprise but are not limited thereto: glycerine (or glycerol), diglycerine, ethylene glycol, diethyleneglycol, propylene glycol, butylene glycol, polyethylene glycols, polypropylene glycols, propanediol, methylpropanediol, sorbitol, mannitol, glucose, saccharose, glucamine, dihydroxyacetone, and mixtures thereof, preferably glycerine.

Preferably, a dispersion of the invention may comprise at least 1%, preferably at least 3% by weight of polyol(s), preferably glycerine, relative to the total weight of said dispersion.

In addition to texture, the dispersions of the invention afford a further advantage compared with «conventional» makeup emulsions, especially foundations, since they allow the use of polyols in particular of glycerine and in high content.

In particular, they can comprise one or more polyols, preferably glycerine, in an amount equal to or higher than 10%, equal to or higher than 20%, equal to or higher than 30%, equal to or higher than 40%, even up to 50% by weight relative to the total weight of said dispersion.

Preparation Method

The dispersions of the invention can be prepared with different methods.

For example, the dispersions of the invention have the advantage that they can be prepared using a simple «non-microfluidic» method, namely by simple emulsification As in a conventional emulsion, an aqueous solution and a fatty solution are prepared separately. It is the addition under agitation of the fatty phase to the aqueous phase which creates the direct emulsion and hence the dispersion of the invention.

The viscosity of the aqueous phase can be controlled, in particular by acting on the amount of anionic polymer (carbomer in particular) and on the pH of the solution. In general, the pH of the aqueous phase is lower than 4.5, which can entail the addition of a third, sodium hydroxide solution (BF) at a last stage to reach a pH of between 5.5 and 6.5.

The viscosity of the aqueous phase and the shear force applied to the mixture are the two main parameters having an influence on the size (and hence the macroscopic nature) and monodispersity of the droplets of the dispersion of the invention.

Those skilled in the art are able to adjust the non-microfluidic method to meet the criterion of mean diameter of the droplets of the dispersion of the invention.

The dispersions of the invention can also be prepared using a microfluidic method. Microfluidic methods able to produce dispersions of the invention are particularly described in WO2012/120043 or WO2015/055748.

In this embodiment, the droplets obtained with a microfluidic method have uniform size distribution.

Preferably, the dispersions of the invention are composed of a population of monodisperse droplets G1, in particular such that they have a mean diameter $\overline{D}$ in the range of 150 µm to 3 000 µm and a coefficient of variation Cv of less than 10%, even less than 3%.

In the present invention, by "monodisperse droplets" it is meant the fact that the population of droplets G1 in the dispersion of the invention has uniform size distribution.

Monodisperse droplets have good monodispersity. Conversely, droplets having poor monodispersity are said to be "polydisperse".

In one embodiment, the mean diameter $\overline{D}$ of the droplets is measured for example by analysis of a photograph of a batch composed of N droplets, using image processing software (Image J). Typically, with this method the diameter is measured in pixels then converted to µm, as a function of the size of the container containing the droplets of the dispersion.

Preferably the value of N is chosen to be equal to or higher than 30 so that this analysis reflects the diameter distribution of the droplets of said emulsion in statistically significant manner. N is advantageously equal to or higher than 100, in particular if the dispersion is polydisperse.

The diameter Di of each droplet is measured and a mean diameter $\overline{D}$ is obtained by calculating the arithmetic mean of these values:

$$\overline{D} = \frac{1}{N}\sum_{i=1}^{N} D_i$$

From these values $D_i$, it is possible to obtain the standard deviation σ of the diameters of the droplets in the dispersion:

$$\sigma = \sqrt{\frac{\sum_{i=1}^{N}(D_i - \overline{D})^2}{N}}$$

The standard deviation σ of a dispersion reflects the distribution of the diameters $D_i$ of the droplets of the dispersion around the mean diameter $\overline{D}$.

With knowledge of the mean diameter $\overline{D}$ and standard deviation σ of a dispersion, it is possible to determine that 95.4% of the population of droplets is found in the diameter range [$\overline{D}$−2σ; $\overline{D}$+2σ] and that 68.2% of the population is found in the range [$\overline{D}$−σ; $\overline{D}$+σ].

To characterize the monodispersity of the dispersion in this embodiment of the invention, the coefficient of variation can be calculated:

$$C_v = \frac{\sigma}{\overline{D}}$$

This parameter reflects the distribution of the diameters of the droplets as a function of the mean diameter thereof.

The coefficient of variation Cv of the diameters of the droplets G1 in this embodiment of the invention is less than 10%, preferably less than 5%, even less than 3%.

Alternatively, monodispersity can be evidenced by placing a sample of dispersion in a bottle of constant circular cross-section. The bottle is gently agitated by rotating it a quarter of a turn within a half-second about the axis of symmetry passing through the bottle, and it is then left to stand for a half-second before performing similar rotation of the bottle in opposite direction; this operation is repeated four times.

The droplets of the dispersed phase organize themselves in crystalline form if they are monodisperse droplets. They are therefore stacked in a pattern that is repeated in the three dimensions. It is then possible to observe regular stacking which indicates good monodispersity, irregular stacking translating polydispersity of the dispersion.

To obtain monodisperse droplets, it is also possible to use the microfluidic technique (Utada et al. MRS Bulletin 32, 702-708 (2007); Cramer et al. Chem. Eng. Sci. 59, 15, 3045-3058 (2004)), and more particularly microfluidic systems of co-flow type (the fluids flow in the same direction) or flow-focusing type (the fluids flow in different directions and typically in opposite direction).

The different fluids and in particular the flow rates thereof can be used in a microfluidic method of the invention using a hydrodynamic mode known as «dripping» (drop-by-drop) or «jetting» (formation of a liquid jet leaving the microfluidic device and fragmentation of the jet in ambient air under the effect of gravity).

The presence in the fatty phase of gelling agent(s) such as previously described, in particular heat-sensitive agents, may necessitate adjustments to the method for preparing a dispersion of the invention. In particular, the preparation method of a dispersion of the invention may comprise a heating step (between 40° C. and 150° C., in particular between 50° C. and 90° C.) to heat at least the fatty phase and optionally the aqueous phase before mixing/contacting said fatty phase with the aqueous phase, and optionally if a «non-microfluidic method» is applied such as mentioned above, this heating is maintained throughout agitation until the desired dispersion is obtained.

In one embodiment, the method for preparing dispersions of the invention comprises a step to form the droplets comprising:

optionally heating an oily fluid F1 and optionally an aqueous fluid FE, to a temperature of between 40° C. and 150° C.;

contacting an aqueous fluid FE and an oily fluid F1 such as defined below; and forming fatty phase droplets composed of an oily fluid F1 dispersed in a continuous aqueous phase composed of fluid FE, said droplets optionally comprising a shell isolating the core of fatty phase droplets of the dispersion.

In one embodiment, fluid F1 is initially prepared by mixing at least one oil and at least one pigment in a content higher than 23.5 weight % relative to the weight of the dispersed fatty phase, optionally at least one first precursor polymer of coacervation e.g. a cationic polymer such as previously defined, at least one gelling agent and/or at least one additional compound such as mentioned above.

In one embodiment fluid FE comprises at least water, optionally in addition at least a second precursor polymer of coacervation, in particular an anionic polymer such as previously defined, at least one base, at least one additional compound, preserving agents and/or other water-soluble products e.g. glycerine such as mentioned above.

In one embodiment, the continuous aqueous phase of the formed dispersion comprises, is even composed of, the aqueous phase of fluid FE. The anionic polymer optionally contained in said fluid FE is especially used to form the shell of the droplets. Said anionic polymer also contributes towards increasing the viscosity of the fluid FE and hence of the continuous aqueous phase.

In one embodiment, a method of the invention in particular the droplet formation step may also comprise a step to inject a solution increasing the viscosity of the continuous aqueous phase of fluid FE. Preferably the viscosity-increasing solution is aqueous. This viscosity-increasing solution is typically injected into the outer aqueous fluid FE after forming the dispersion of the invention, and hence after forming the droplets.

In one embodiment, the viscosity-increasing solution comprises a base in particular an alkaline hydroxide such as sodium hydroxide.

In one embodiment, the temperature of the above-mentioned heating step is between 50° C. and 80° C., preferably from 50° C. to 70° C., and more preferably from 55 to 65° C.

Depending on the pigment(s) used, a method to prepare a dispersion of the invention can comprise the steps of:

a) providing at least one pigment optionally pre-treated with an additive improving the dispersibility of the pigment; then b) optionally grinding said at least one pigment, said grinding preferably being performed when the at least one pigment is not pre-treated;

c) dispersing the at least one pigment in at least one oily fluid FI;

e) optionally, heating said oily fluid F1 and optionally the aqueous fluid FE, to a temperature of between 40° C. and 150° C., preferably from 50° C. to 90° C.;

f) placing the aqueous fluid FE in contact with the oily fluid FI; and g) forming droplets of the fatty phase composed of oily fluid F1 dispersed in a continuous aqueous phase composed of aqueous fluid FE, said droplets optionally comprising a shell isolating the core of fatty phase droplets of the dispersion, where:

the oily fluid F1 comprises at least one oil and optionally at least one cationic polymer such as previously defined, amodimethicone in particular, at least one gelling agent and/or at least one additional compound such as mentioned above; and the aqueous fluid FE comprises at least water and optionally at least one anionic polymer such as previously defined, a carbomer in particular, and/or at least one additional compound such as above-mentioned.

Uses

Preferably a dispersion of the invention can be used directly after the aforementioned preparation methods, as a composition and in particular a cosmetic composition. The dispersion of the invention, when prepared with a microfluidic method such as described above, can also be used as a composition particularly a cosmetic composition after separation of the droplets and redispersion thereof in a second suitable phase.

The invention also concerns the use of at least one dispersion of the invention for addition to a cosmetic composition.

The dispersions of the invention can particularly be used in the cosmetic field.

The invention also concerns a cosmetic composition, preferably a makeup composition, comprising at least one dispersion such as defined above.

The cosmetic compositions of the invention, in addition to the above-mentioned ingredients, may also comprise at least one physiologically acceptable medium.

The invention therefore also concerns a composition comprising at least one dispersion such as defined above in association with a physiologically acceptable medium.

By "physiologically acceptable medium" it is meant to designate a medium particularly suitable for application of a composition of the invention onto keratin material, and in particular the skin, lips, nails, eyelashes or eyebrows and preferably the skin.

The physiologically acceptable medium is generally adapted to the type of substrate onto which the composition is to be applied and to the appearance the composition is to have when packaged.

The presence of a physiologically acceptable medium can contribute towards improved storage and/or preserved integrity over time of the droplets of a dispersion of the invention.

In one embodiment, the physiologically acceptable medium is in the form of an aqueous gel having adapted viscosity, in particular to ensure suspension of the droplets of the invention.

In one embodiment the cosmetic compositions are used for makeup and/or care of keratin material in particular the skin.

The cosmetic compositions of the invention can be care products, sunscreen products, cleansing (makeup removal) products, hygiene or makeup products.

These compositions are therefore intended to be applied in particular to the skin, lips or hair.

The present invention therefore also concerns the non-therapeutic cosmetic use of a dispersion or composition of the invention as makeup, hygiene, cleansing and/or care product of keratin material, of the skin in particular.

In one embodiment, the dispersions or compositions of the invention are in the form of a foundation, makeup removal product, face and/or body and/or hair care product, anti-ageing care product, sunscreen, oily skin care product, whitening care product, hydrating care product, BB cream, tinted cream or foundation, face and/or body cleansing product, shower gel or shampoo, preferably a foundation.

A dispersion or composition of the invention can in particular be a sunscreen composition, care cream, or serum or deodorant.

The dispersions or compositions of the invention can be in various forms, in particular a cream, balm, lotion, serum, gel, gel-cream or mist.

In particular, a dispersion or composition of the invention is a care and/or makeup composition of keratin material, of the skin in particular, and especially a makeup composition.

More particularly, a dispersion or composition of the invention can be a mascara for example, or complexion product e.g. a foundation an eye-liner, eyeshadow, blusher, lip product e.g. a lipstick or lip-gloss, an optionally liquid soap, shampoo, conditioner, nail varnish, preferably an eyeshadow, complexion products or lip products. The dispersion or composition of the invention can be in the form of a monophase or biphasic lotion, emulsion, gel, stick or cream.

A dispersion or composition of the invention is preferably in the form of a foundation to be applied to the face or neck, a dark circle concealer, colour corrector, tinted cream or makeup base for the face, or makeup composition for the body.

The present invention also concerns a non-therapeutic cosmetic treatment method, in particular a makeup and/or care method, preferably a makeup method of keratin material in particular the skin, lips or hair, comprising at least one step to apply to said keratin material at least one dispersion or composition of the invention.

In particular, the present invention concerns a non-therapeutic cosmetic treatment method, in particular a makeup method of the skin comprising a step to apply to the skin at least one dispersion or composition of the invention.

The present invention also concerns the use of a dispersion or composition of the invention to improve the properties of a cosmetic composition, in particular a makeup composition and more particularly a foundation, in terms of:
- colour shade intensity: the inventors have observed on application to keratin material and in particular the skin, and for equivalent pigment type and percentage, that a dispersion of the invention induces a more intense colour shade, even a darker shade than a conventional foundation; this observation would seem to indicate that a dispersion of the invention allows better revealing of pigments;
- progressive (or evolving) makeup result: the inventors have observed after application to keratin material, in particular the skin, that the colour shade initially faint gradually becomes more intense as mentioned above;
- freshness and/or hydration;
- kinetic stability;
- long-wearing of the makeup effect, in particular long-lasting coverage; and
- good flawless coverage of colour imperfections and/or surface imperfections combined with a sensation of lightness, freshness and hydration on application which has good slip without any sensation of oiliness and/or tack.

In the entire description including the claims, the expression «comprising a/an» is to be construed as a synonym of «comprising at least one», unless otherwise specified.

The expressions «of between . . . and . . . », «from . . . to . . . » and «ranging from . . . to . . . » are to be understood to include the limits unless otherwise specified.

The quantities of the ingredients given in the examples are expressed in weight percent relative to the total weight of the composition, unless otherwise stated.

The following examples illustrate the present invention without limiting the scope thereof.

EXAMPLES

Unless otherwise specified, the compositions described below can be obtained with a non-microfluidic method or a microfluidic method such as described above or in WO 2017/046305 for the microfluidic method.

Example 1: Dispersion of the Invention—Foundation

The compositions of the phases (fluids) are the following:

| Name | | INCI name | % w/w | Phases |
|---|---|---|---|---|
| AQUEOUS GEL PHASE (=OF) | | | 100.00 | A |
| Reverse osmosis water (RO water) | / | Aqua | Q.S.* | A1 |
| MICROCARE PE | Thor | PHENOXYETHANOL, AQUA | 0.87 | A1 |
| MICROCARE EMOLLIENT PTG | Thor | PENTYLENE GLYCOL, AQUA | 2.17 | A1 |
| CARBOPOL ETD2050 | Lubrizol | CARBOMER | 0.20 | A3 |
| ALCASEALAN | Hakuto | ALCALIGENES POLYSACCHARIDES | 0.02 | A2 |
| GLYCERINE CODEX | Interchimie | GLYCERIN, AQUA | 3.26 | A4 |
| GLUCAM E20 HUMECTANT | Lubrizol | METHYL GLUCETH-20 | 3.26 | A4 |
| UNITAMURON H-22 | Induchem | BUTYLENE GLYCOL, TAMARINDUS INCA SEED GUM, PHENOXYETHANOL | 5.43 | A5 |
| EDETA BD | BASF | DISODIUM EDTA | 0.03 | A1 |
| SODIUM HYDROXIDE PELLETS PRS CODEX | Panreac | SODIUM HYDROXIDE | 0.03 | A6 |
| OILY PHASE (=IF) | | | 100.00 | B |
| ALPHAFLOW 20 | The innovation company | HYDROGENATED POLYDECENE | Q.S.* | B1/B2 |
| BENTONE GEL EUG V | Elementis | OCTYLDODECANOL AND DISTEARDIMONIUM HECTORITE AND PROPYLENE CARBONATE | 20.00 | B2 |
| PELEMOL PHS-8 | Phoenix Chemical | POLYHYDROXYSTEARIC ACID | 3.65 | B3 |
| ASL-1 TIO2 CR-50 | Daito Kasei | CI77891, Aluminium hydroxide, Sodium Lauroyl glutamate, Lysine, Magnesium chloride | 38.82 | B3 |
| ASL-1 YELLOW LL-100P | Daito Kasei | CI 77492, Sodium Lauroyl glutamate, Lysine, Magnesium chloride | 3.85 | B3 |
| ASL-1 RED R-516P | Daito Kasei | CI 77491, Sodium Lauroyl glutamate, Lysine, Magnesium chloride | 1.02 | B3 |
| ASL-1 BLACK BL-100P | Daito Kasei | CI 77499, Sodium Lauroyl glutamate, Lysine, Magnesium chloride | 0.07 | B3 |
| Parfum | — | Fragrance | 0.20 | B4 |
| CAS-3131 PILOT | Nusil | AMODIMETHICONE | 0.50 | B1 |

*Q.S.: as much as is sufficient

Preparation Protocol:

For OF:

A1: Phenoxyethanol, Pentyleneglycol and EDTA are incorporated in water. The mixture is stirred for 5 min.

A2: Alcasealan is added under rotor stator agitation (4500 rpm) for 15 min.

A3: The carbomer is then dispersed in the preceding mixture under agitation for 30 minutes using an impeller of disperser blade type.

A4: The glycerine and Glucam E20 are mixed together and this mixture added under continued agitation for 10 min.

A5: Unitamuron H-22 is added to the mixture under disperser blade agitation for 20 min.

A6: Sodium hydroxide is added and the solution mixed for 10 minutes.

For IF:

B1: Amodimethicone is added to a portion (¾) of ALPHAFLOW 20 and mixed using a magnetic stir bar for 5 min (=mixture B1).

B2: In a beaker, the BENTONE solution is weighed. Using a pipette, mixture B1 is added to the BENTONE solution and stirred with a spatula (=mixture B2).

B3: In another beaker, the 4 ASL pigments are weighed. The PELEMOL PHS-8 is weighed in a dish with the remaining portion (¼) of ALPHAFLOW and heated to 45° C. When melted, these are incorporated in the beaker comprising the pigments followed by homogenisation with a spatula (=mixture B3).

Mixture B3 is incorporated in mixture B2.

B4: The fragrance is added under agitation until homogenisation.

Parameters for the Non-Microfluidic Method 276 g of OF are poured into a 400 ml beaker under agitation in a Rayneri mixer (impeller: disperser blade 650 mm in diameter; speed: 250 rpm).

Under agitation, 24 g of IF are added.

This mixing is continued for 15 minutes.

Parameters for the Microfluidic Method:

In these tests, the following flow rates and parameters were used:

| Parameters of microfluidic method | Flow rate (per nozzle; in ml/h) |
|---|---|
| IF | 20 |
| OF | 180 |
| BF** | 21.6 |

**Optionally, a viscosity-increasing solution (BF) can be added to the continuous phase to improve the suspension of the droplets of the phase dispersed in the continuous phase, in particular such as described in WO2015055748. In particular this BF is a sodium hydroxide solution (NaOH).

The entire method and all the phases are implemented are at ambient temperature.

Results:

Having regard to the cosmetic end use, namely a foundation, the dispersion of the invention has unique visual impact, namely brown macroscopic droplets dispersed in a transparent suspensive aqueous phase.

After application, the makeup result is unique since it is progressive (or evolving). First a faint colour shade of the skin is observed, which gradually becomes more intense. The final colour shade appears after about 45 seconds after application to the skin. The long-wearing property of this colour shade is also particularly satisfying.

In addition, an improved colour shade is observed. The makeup result of a dispersion of the invention on the skin unexpectedly imparts a particularly intense colour shade having regard to the percentage of pigments in said dispersion. This observation can be translated as excellent revealing of the pigments contained in IF in the form of macroscopic droplets.

In addition to a particularly satisfactory makeup result, the dispersion gives rise to satisfactory sensory feel on application, in particular in terms of freshness and hydration.

In general, it is observed that the dispersion according to Example 1 provides good flawless coverage of colour imperfections and/or surface imperfections combined with a sensation of lightness, freshness and hydration on application which has good slip without any sensation of oiliness and/or tack.

Finally, the dispersion in Example 1, in particular the colour shade and coverage thereof, remains stable (in particular no dephasing, opacification, colour change) after 3 months at ambient temperature and atmospheric pressure. This dispersion therefore has satisfactory resistance properties against sweat and moisture.

For the dispersion obtained with a microfluidic method, the droplets having a diameter equal to or greater than 150 μm represent a volume equal to or greater than 60%, even equal to or greater than 70% of the total volume of the dispersed phase, and at least 60% of the droplets have a mean diameter equal to or greater than 150 μm, even equal to or greater than 250 μm.

Example 2: Non-Pigment and Pigmented Dispersions

Example 2 describes two compositions 2A and 2B having the following respective phase (fluid) compositions:

| | | | 2A | | 2B | |
|---|---|---|---|---|---|---|
| Name | | INCI name | % w/w | Phases | % w/w | Phases |
| AQUEOUS GEL PHASE (=OF) | | | 100.00 | A | 100.00 | A |
| RO water | / | Aqua | Q.S.* | A1 | Q.S.* | A1 |
| MICROCARE PE | Thor | PHENOXYETHANOL, AQUA | 0.87 | A1 | 0.87 | A1 |
| MICROCARE EMOLLIENT PTG | Thor | PENTYLENE GLYCOL, AQUA | 2.17 | A1 | 2.17 | A1 |
| CARBOPOL ETD2050 | Lubrizol | CARBOMER | 0.20 | A3 | 0.20 | A3 |
| ALCASEALAN | Hakuto | ALCALIGENES POLYSACCHARIDES | 0.02 | A2 | 0.02 | A2 |

-continued

| Name | | INCI name | 2A % w/w | Phases | 2B % w/w | Phases |
|---|---|---|---|---|---|---|
| GLYCERINE CODEX | Interchimie | GLYCERIN, AQUA | 3.26 | A4 | 3.26 | A4 |
| GLUCAM E20 HUMECTANT | Lubrizol | METHYL GLUCETH-20 | 3.26 | A4 | 3.26 | A4 |
| UNITAMURON H-22 | Induchem | BUTYLENE GLYCOL, TAMARINDUS INCA SEED GUM, PHENOXYETHANOL | 5.43 | A5 | 5.43 | A5 |
| EDETA BD | BASF | DISODIUM EDTA | 0.03 | A1 | 0.03 | A1 |
| SODIUM HYDROXIDE PELLETS PRS CODEX | Panréac | SODIUM HYDROXIDE | 0.03 | A6 | 0.03 | A6 |
| OILY PHASE (=IF) | | | 100.00 | B | 100.00 | B |
| DUB ININ A | Stearinerie Dubois | Isononyl Isononanoate | Q.S.* | B1 | Q.S.* | B1 |
| DUB 810C/MB | Stearinerie Dubois | Coco-Caprylate/Caprate | 10.00 | B1 | 10.00 | B2 |
| NIKKOL MEADOWFOAM OIL | NIKKO CHEMICALS | LIMNANTHES ALBA SEED OIL, TOCOPHEROL | 18 | B1 | 10 | B2 |
| Estogel M | Poplymer Expert | Castor Oil/IPDI Copolymer (70-90%), Caprylic/Capric Triglyceride (10-30%) | 8 | B2 | 8 | B1 |
| CAS-3131 PILOT | Nusil | AMODIMETHICONE | 0.20 | B3 | 0.20 | B3 |
| ASL-1 TIO2 CR-50 | Daito Kasei | CI77891, Aluminium hydroxide, Sodium Lauroyl glutamate, Lysine, Magnesium chloride | 0 | | 38.82 | B2 |
| ASL-1 YELLOW LL-100P | Daito Kasei | CI 77492, Sodium Lauroyl glutamate, Lysine, Magnesium chloride | 0 | | 3.85 | B2 |
| ASL-1 RED R-516P | Daito Kasei | CI 77491, Sodium Lauroyl glutamate, Lysine, Magnesium chloride | 0 | | 1.02 | B2 |
| ASL-1 BLACK BL-100P | Daito Kasei | CI 77499, Sodium Lauroyl glutamate, Lysine, Magnesium choride | 0 | | 0.07 | B2 |

*Q.S.: as much as is sufficient

Preparation Protocol:

For OF: same protocol as described in Example 1.

For IF of composition 2A:

B1: DUB ININ A, DUB 810C/MB and NIKKOL MEADOWFOAM OIL are mixed at ambient temperature for 5 minutes.

B2: Estogel M is added to B1. The dispersion is left under agitation for 30 minutes using a disperser blade at 80° C. until homogenisation.

B3: Finally, CAS-3131 PILOT is added to mixture B2 and agitation continued for 3 minutes at 80° C.

For IF of composition 2B:

B1: DUB ININ A and Estogel M are mixed at 80° C. for 30 minutes using a disperser blade until homogenisation.

B2: In another container, DUB 810C/MB and NIKKOL MEADOWFOAM OIL are mixed, the 4 ASL pigments are added and homogenised with a spatula (=mixture B2).

Mixture B2 is gently incorporated in mixture B1 under gentle agitation at 80° C. (=mixture X).

B3: Finally, CAS-3131 PILOT is added to mixture X and agitation continued for 3 minutes at 80° C.

Parameters of the Non-Microfluidic Method 276 g of OF are poured into a 400 ml beaker under agitation at ambient temperature in Rayneri apparatus (impeller: disperser blade of diameter 650 mm; mixing speed: 100 rpm).

Under agitation, the addition is made of 24 g of IF which has been held at 80° C.

This agitation is continued for 10 minutes.

Parameters of the Microfluidic Method:

In these tests, the following flow rates and parameters were used:

| Parameters of the microfluidic method | Flow rate (per nozzle; in ml/h) |
|---|---|
| IF | 20 |
| OF | 180 |
| BF** | 21.6 |

**Optionally, the addition can be made of a solution (BF) increasing the viscosity of the continuous phase to improve the suspension of the droplets of the dispersed phase in the continuous phase, in particular such as described in WO2015055748. This BF is particularly a sodium hydroxide (NaOH) solution.

The microfluidic device comprises a first part in which contacting is performed under heat (between 75° C. and 85-90° C.) between IF (=dispersed fatty phase) and OF (=continuous aqueous phase) to form the composition, and a second part ensuring rapid cooling of the composition thus formed to accelerate the gelling kinetics of the droplets and thereby prevent risks of post-formation coalescence of the droplets (cooling temperature: between 5° C. and 28° C.).

Hot water bath: 80° C.
Syringe heater for IF: 80° C.
Cold bath: 17.5° C.

Results:

The results and advantages of composition 2B are the same as those in Example 1.

For dispersions 2A and 2B obtained with a microfluidic method, the droplets having a diameter equal to or greater than 150 µm represent a volume equal to or greater than 60%, even equal to or greater than 70% of the total volume of the dispersed phase, and at least 60% of the droplets have a mean diameter equal to or greater than 150 µm, even equal to or greater than 250 µm.

In addition, Example 2, in particular dispersion 2A, gives information on the properties of Estogel, in particular:

gelling of an oily phase whilst maintaining very good transparency of this oily phase;

improved stabilisation of a dispersion and mechanical strength of the droplets, in particular when this dispersion is macroscopic i.e. where the droplets of a dispersed phase are of large size as described above;

ensured good dispersion of pigments in the oily phase;

reduced sensation of tack, greasiness and adhesion of the oily phase to the skin (satisfactory, even improved sensory feel of the formula on application); and maintained satisfactory sprayability of the formula, even at high Estogel concentrations.

Example 3: Comparatives

Compositions 3A, 3B and 3B described below were obtained using a microfluidic method such as described in FR1857625, the phase (fluid) compositions being as follows:

| Name | | INCI name | 2A comparative % w/w | Phases | 2B of the invention % w/w | Phases | 2C of the invention % w/w | Phases |
|---|---|---|---|---|---|---|---|---|
| AQUEOUS GEL PHASE (=OF) | | | 100.00 | A | 100.00 | A | 100.00 | A |
| RO water | / | Aqua | Q.S.* | A1 | Q.S.* | A1 | Q.S.* | A1 |
| MICROCARE PE | Thor | PHENOXYETHANOL, AQUA | 1.14 | A1 | 1.14 | A1 | 1.14 | A1 |
| PENTIOL GREEN + | Minasolve | PENTYLENE GLYCOL, AQUA | 2.85 | A1 | 2.85 | A1 | 2.85 | A1 |
| CARBOPOL ETD2050 | Lubrizol | CARBOMER | 0.26 | A3 | 0.26 | A3 | 0.26 | A3 |
| ALCASEALAN | Hakuto | ALCALIGENES POLYSACCHARIDES | 0.03 | A2 | 0.03 | A2 | 0.03 | A2 |
| GLYCERINE CODEX | Interchimie | GLYCERIN, AQUA | 4.28 | A4 | 4.28 | A4 | 4.28 | A4 |
| UNITAMURON H-22 | Induchem | BUTYLENE GLYCOL, TAMARINDUS INCA SEED GUM, PHENOXYETHANOL | 7.14 | A5 | 7.14 | A5 | 7.14 | A5 |
| EDETA BD | BASF | DISODIUM EDTA | 0.04 | A1 | 0.04 | A1 | 0.04 | A1 |
| SODIUM HYDROXIDE PELLETS PRS CODEX | Panréac | SODIUM HYDROXIDE | 0.03 | A6 | 0.03 | A6 | 0.03 | A6 |
| OILY PHASE (=IF) | | | 100.00 | B | 100.00 | B | 100.00 | B |
| MYRITOL 318 | Ami Chimie | CAPRYLIC CAPRIC TRIGLYCERIDES | Q.S.* | B1 | Q.S.* | B1 B4 | Q.S.* | B1 B4 B5 |
| ISODODECANE | INEOS | ISODODECANE | 10.00 | B2 | 10.00 | B2 | 10.00 | B2 |
| MEADOWFOAM SEED OIL | FANCOR | LIMNANTHES ALBA (MEADOWFOAM) SEED OIL | 13.30 | B2 | 13.30 | B2 | 13.30 | B2 |
| COSMEDIA GEL CC | Elementis | DICAPRYLYL CARBONATE AND STEARALKONIUM HECTORITE AND PROPYLENE CARBONATE | 8.33 | B2 | 8.33 | B2 | 8.33 | B2 |
| PELEMOL PHS-8 | Phoenix Chemical | POLYHYDROXYSTEARIC ACID | 0 | B5 | 0 | B5 | 1.67 | B5 |
| SUNSHINE FINE WHITE | Sunchemicals | SYNTHETIC FLUORPHLOGOPITE | 3.33 | B3 | 3.33 | B3 | 3.33 | B3 |
| CAS-3131 PILOT | Nusil | AMODIMETHICONE | 0.33 | B1 | 0.33 | B1 | 0.33 | B1 |
| ASL-1 TIO2 CR-50 | Daito Kasei | CI77891, Aluminum hydroxide, Sodium Lauroyl glutamate, Lysine, Magnesium chloride | 0 | B4 | 33.32 | B4 | 33.32 | B4 |

-continued

| Name | INCI name | 2A comparative % w/w | 2A comparative Phases | 2B of the invention % w/w | 2B of the invention Phases | 2C of the invention % w/w | 2C of the invention Phases |
|---|---|---|---|---|---|---|---|
| ASL-1 YELLOW LL-100P | Daito Kasei | CI 77492, Sodium Lauroyl glutamate, Lysine, Magnesium chloride | 0 | B4 | 4.86 | B4 | 4.86 | B4 |
| ASL-1 RED R-516P | Daito Kasei | CI 77491, Sodium Lauroyl glutamate, Lysine, Magnesium chloride | 0 | B4 | 1.22 | B4 | 1.22 | B4 |
| ASL-1 BLACK BL-100P | Daito Kasei | CI 77499, Sodium Lauroyl glutamate, Lysine, Magnesium choride | 0 | B4 | 0.60 | B4 | 0.60 | B4 |

*Q.S.: as much as is sufficient

Preparation Protocol:

For OF: same protocol as described in Example 1.

For IF:

B1: Depending on the compositing under consideration, amodimethicone is added to all or part (¾) of MYRITOL 318 then mixed with a magnetic stir bar for 5 min (=mixture B1).

B2: In a beaker, COSMEDIA GEL CC, ISODODECANE and MEADOWFOAM SEED OIL are mixed together. Using a pipette, mixture B1 is slowly added to the aforementioned beaker and mixed with a spatula (=mixture B2).

B3: Under agitation, SUNSHINE FINE WHITE is added to mixture B2 (=mixture B3).

B4: If used, in another beaker the 4 ASL pigments are weighed with the remaining portion of MYRITOL 318 (or ¼ of PELEMOL PHS-8 if used), and this mixture is slowly added to mixture B3 (=mixture B4).

B5: If used, the PELEMOL PHS-8 is weighed in a dish with the remaining portion (¼) of MYRITOL 318 and heated to 45° C. Once melted, it is incorporated in the beaker comprising the pigments and homogenised with a spatula (=mixture B5). Mixture B5 is incorporated in mixture B4.

Parameters of the Microfluidic Method:

In these tests, the following flow rates were used:

| Phase | Flow rate (per buse; in ml/h) |
|---|---|
| IF | 142.8 |
| OF | 288 |
| BF | 15.2 |

BF = 10% sodium hydroxide solution (NaOH).

Results:

Samples of compositions 3A, 3B and 3C were collected. From these samples and using cellSens software, the diameter of 30 droplets was measured under a microscope.

FIG. 1 shows the droplet size distribution of these compositions 3A, 3B and 3C.

This comparative example confirms that the use of pigments in the fatty phase of a dispersion of the invention (composition 3B) leads to a reduction in droplet size compared with one same dispersion devoid of any pigment (composition 3A).

This comparative example also shows that the addition of PELEMOL (composition 3C) allows this reduction in droplet size to be offset (observed with composition 3B), and even allows a droplet size to be obtained that is greater than that obtained with composition 3A.

What is claimed is:

1. A dispersion containing a dispersed phase comprising droplets and a continuous aqueous phase, wherein the droplets comprise at least one fatty phase,
    wherein the fatty phase comprises at least one pigment in a content higher than 23.5 weight % relative to the weight of the fatty phase, and wherein the fatty phase also comprises at least one lipophilic gelling agent,
    wherein said lipophilic gelling agent is selected from the group consisting of: organic or mineral, polymeric or molecular lipophilic gelling agents, and mixtures thereof; and wherein the lipophilic gelling agent is not a polyorganosiloxane;
    wherein said mineral lipophilic gelling agent is selected from the group consisting of: hectorites modified by $C_{10}$ to $C_{22}$ ammonium chloride, hectorite modified by distearyl dimethyl ammonium chloride, hectorite modified by distearyl dimethyl ammonium chloride, benzalkonium and quaternium-18 bentonites, and clays modified by stearyldimethylbenzoylammonium chloride, and
    wherein the droplets have a diameter larger than 500 μm and represent a volume equal to or greater than 60% of the total volume of the dispersed phase, and/or at least 60% of the droplets have a mean diameter larger than 500 μm,
    wherein the droplets also comprise a shell, said shell comprising at least one anionic polymer and at least one cationic polymer, and
    wherein the dispersion does not comprises a surfactant.

2. The dispersion according to claim 1, wherein the fatty phase comprises between 24% and 60% by weight of pigment(s) relative to the total weight of the fatty phase.

3. The dispersion according to claim 1, comprising between 1% and 76.49% by weight of oil(s) relative to the total weight of the fatty phase.

4. The dispersion according to claim 1, wherein the droplets comprise a core that is liquid or at least partly gelled or at least partly thixotropic, and optionally a shell fully encapsulating said core, said core being monophasic or comprising an intermediate droplet of an intermediate phase, the intermediate phase being placed in contact with the continuous aqueous phase or with the shell if any, and at least one inner droplet of an inner phase arranged in the intermediate droplet,
    the pigment(s) being contained in the intermediate phase and/or inner phase.

5. The dispersion according to claim 1, comprising from 0.5% to 70% by weight of lipophilic gelling agent(s) relative to the total weight of the fatty phase.

6. The dispersion according to claim 1, wherein the cationic polymer is a silicone polymer modified by a primary, secondary or tertiary amine function.

7. The dispersion according to claim 1, comprising from 0.5% to 5% by weight of cationic polymer(s) relative to the total weight of the fatty phase.

8. The dispersion according to claim 1 wherein the anionic polymer is a polymer comprising monomer units comprising at least one carboxylic acid chemical function.

9. The dispersion according to claim 1, wherein:
   the continuous aqueous phase also comprises at least one blurring effect filler and/or at least one colouring agent selected from the group formed by pigments, colouring agents, materials having optical effect, and mixtures thereof; and/or
   the fatty phase also comprises at least one blurring effect filler and/or at least one colouring agent selected from the group formed by colouring agents, materials having optical effect, and mixtures thereof.

10. The dispersion according to claim 1, wherein the cationic polymer has the following formula:

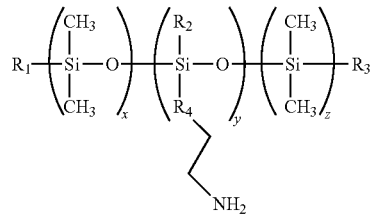

where:

$R_1$, $R_2$ and $R_3$, are each independently OH or $CH_3$;

$R_4$ is a group —$CH_2$— or a group —X—NH— where X is a C3 or C4 divalent alkylene radical;

x is an integer between 10 and 5 000;

y is an integer between 1 and 1 000; and z is an integer between 0 and 10.

11. The dispersion according to claim 1, wherein the anionic polymer is hydrophilic and the cationic polymer is lipophilic.

12. The dispersion according to claim 1, wherein the lipophilic gelling agent is selected from the group consisting of: polymeric organic lipophilic gelling agents selected from the group consisting of: ethylcellulose; galactomannans comprising one to six hydroxyl groups per monosaccharide unit substituted by a saturated or unsaturated alkyl chain, block copolymers of diblock, triblock or radial polystyrene/polyisoprene, polystyrene/polybutadiene, polystyrene/co-poly(ethylene-propylene) or polystyrene/copoly(ethylenebutylene), and mixtures of triblock and radial copolymers in isododecane; polyacrylates; esters of dextrin and fatty acid(s); esters of glycerol and fatty acid(s); esters of inulin and fatty acid(s); polyamides, and mixtures thereof.

13. The dispersion according to claim 1, wherein the lipophilic gelling agent is Castor oil/IPDI Copolymer and Caprylic/Capric triglyceride.

14. The dispersion according to claim 1, wherein the cationic polymer is amodimethicone.

* * * * *